(12) United States Patent
Koberling et al.

(10) Patent No.: US 7,807,808 B2
(45) Date of Patent: Oct. 5, 2010

(54) BACTERIA WITH INCREASED LEVELS OF PROTEIN SECRETION, NUCLEOTIDE SEQUENCES CODING FOR A SECA PROTEIN WITH INCREASED LEVELS OF PROTEIN SECRETION, AND METHOD FOR PRODUCING PROTEINS

(75) Inventors: Oliver Koberling, Castelnuovo Berardenga (IT); Roland Freudl, Duren (DE)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 12/615,209

(22) Filed: Nov. 9, 2009

(65) Prior Publication Data

US 2010/0184142 A1  Jul. 22, 2010

Related U.S. Application Data

(62) Division of application No. 10/544,755, filed as application No. PCT/DE2004/001107 on May 28, 2004, now Pat. No. 7,655,754.

(30) Foreign Application Priority Data

Jun. 2, 2003  (DE) ................................ 103 25 026

(51) Int. Cl.
| | |
|---|---|
| C12N 15/11 | (2006.01) |
| C12N 15/63 | (2006.01) |
| C12N 15/09 | (2006.01) |
| C12N 9/00 | (2006.01) |
| C12N 9/14 | (2006.01) |
| C12N 9/10 | (2006.01) |
| C12N 9/12 | (2006.01) |
| C12N 9/20 | (2006.01) |
| C12N 9/26 | (2006.01) |
| C12N 9/48 | (2006.01) |
| C12N 9/90 | (2006.01) |
| C12P 1/00 | (2006.01) |
| C12P 21/06 | (2006.01) |
| C12P 21/04 | (2006.01) |
| C12P 21/02 | (2006.01) |
| C07H 21/04 | (2006.01) |

(52) U.S. Cl. ................... 536/23.1; 435/243; 435/252.1; 435/252.3; 435/252.31; 435/252.32; 435/320.1; 435/41; 435/69.1; 435/71.1; 435/71.2; 435/69.4; 435/69.5; 435/69.6; 435/183; 435/195; 435/198; 435/201; 435/212; 435/233; 435/193; 435/194; 536/23.7

(58) Field of Classification Search ........................ None
See application file for complete search history.

(56) References Cited

FOREIGN PATENT DOCUMENTS

EP  0 892 064 A2  1/1999
EP  0 892 064 A3  1/2000

OTHER PUBLICATIONS

Baud et al., "Allosteric Communication Between Signal Peptides and the SecA Protein DEAD Motor ATPase Domain," *The Journal of Biological Chemistry*, 277(16):13724-13731 (2002).
Freudl et al., "Proteinsekretion bei Gram-positiven Bakterien: Molekulare Grundlagen und biotechnologische Aspekte," *Biospektrum* 4(1):29-33 (1998).
Jarosik et al., "Isolation and Analysis of Dominant *secA* Mutations in *Escherichia coli*," *Journal of Bacteriology*, 173(2):860-868 (1991).
Keilhauer et al., "Isoleucine Synthesis in *Corynebacterium glutamicum*: Molecular Analysis of the *ilvB-ilvN-ilvC* Operon," *Journal of Bacteriology*, 175(17):5595-5603 (1993).
Kisselev, "Polypeptide Release Factors in Prokaryotes and Eukaryotes: Same Function, Different Structure," *Structure*, 10: 8-9 (2002).
Klein et al., "Functional Characterization of the *Staphylococcus carnosus* SecA Protein in *Escherichia coli* and *Bacillus subtilis* secA Mutant Strains," *FEMS Microbiology Letters*, 131:271-277 (1995).
Liebl et al., Transfer of *Brevibacterium divaricatum* DSM 20297$^T$, "*Brevibacterium flavum*" DSM 20411, "*Brevibacterium lactofermentum*" DSM 20412 and DSM 1412, and *Corynebacterium lilium* DSM 20137$^T$ to *Corynebacterium glutamicum* and Their Distinction by rRNA Gene Restriction Patterns," International Journal of Systematic Bacteriology, 41(2):255-260 (1991).
Matsumoto et al., "Genetic Dissection of SecA: Suppressor Mutations Against the *secY205* Translocase defect," *Genes to Cells*, 5:991-999 (2000).
Sousa et al., "The *ARO4* gene of *Candida albicans* encodes a tyrosine-sensitive DAHP synthase : evolution, functional conservation and phenotype of Aro3p-, Aro4p-deficient mutants," *Microbiology*, 148(Pt5):1291-1303 (2002).
van der Wolk et al., "Identification of the Magnesium-binding Domain of the High-affinity ATP-binding Site of the *Bacillus subtilis* and *Escherichia coli* SecA Protein," *Journal of Biological Chemistry*, 270(32):18975-19892, (1995).
Wishart et al., "A Single Mutation Converts a Novel Phosphotyrosine Binding Domain into a Dual-specificity Phosphatase," *Journal of Biological Chemistry*, 270(45):26782-26785, (1995).
Witkowski et al., "Conversion of a β-Ketoacyl Synthase to a Malonyl Decarboxylase by Replacement of the Active-Site Cysteine with Glutamine," *Biochemistry*, 38:11643-11650, (1999).

*Primary Examiner*—Suzanne M Noakes
*Assistant Examiner*—Jae W Lee

(57) ABSTRACT

The invention relates to bacteria that have increased levels of protein secretion due to genetic modification, to nucleotide sequences and gene structures containing at least one gene coding for a SecA protein having increased levels of protein secretion, to a SecA having increased levels of protein secretion, and to a method for producing desired proteins using the inventive bacteria. The invention also relates to nucleic acids coding for a SecA protein having increased levels of protein secretion, containing a SecA gene sequence or allele, a SecA homologue or derivative, or nucleotide sequences hybridising therewith and comprising at least one mutation. Surprisingly, just one mutation in a nucleotide of a SecA gene leads to increased levels of protein secretion or to protein secretion for the first time.

15 Claims, 7 Drawing Sheets

US 7,807,808 B2

BACTERIA WITH INCREASED LEVELS OF PROTEIN SECRETION, NUCLEOTIDE SEQUENCES CODING FOR A SECA PROTEIN WITH INCREASED LEVELS OF PROTEIN SECRETION, AND METHOD FOR PRODUCING PROTEINS

This application is a divisional application of U.S. Ser. No. 10/554,755 filed on Oct. 4, 2006 which is U.S. Pat. No. 7,655,754, issued on Feb. 2, 2010 which claims priority under 35 USC §371 to WO 04/108932 (PCT/DE2004/001107), with an international filing date of May 28, 2004, which claims priority to DE 103 25 026.3, filed Jun. 6, 2003.

This invention relates to bacteria that on the basis of genetic modification display increased secretion of proteins, nucleotide sequences as well as plasmids that contain at least one gene, which codes for a SecA protein with increased secretion for proteins, a SecA with increased protein secretion as well as a method for the production of the desired proteins using the invention-based bacteria.

Gram-positive bacteria (above all, various *Bacillus* species) can discharge proteins in large quantities into the surrounding culture medium. This ability has been used for a long time for the industrial procurement of a plurality of secreted enzymes (such as, for example, amylases, proteases, lipases). The production strains that are used in industry for these processes are optimized by repeated, non-directed mutagenesis and subsequence screening for an increased exoenzyme production, something that can lead to yields of several grams of enzyme per liter of culture supernatant. Most of the time, the causes of the increased productivities of these strains are not known. Various attempts to use gram-positive bacteria as host organisms for the secretory procurement of heterologous proteins frequently yielded only a disappointing result. The yields, thus obtained in the overwhelming majority of cases, turned out to be definitely less than the quantities that can be attained from the secretion of homologous exoproteins. One of the reasons for this is the inefficient or entirely missing transport of the heterologous protein via the cytoplasm membrane [1-4].

Figure 1:
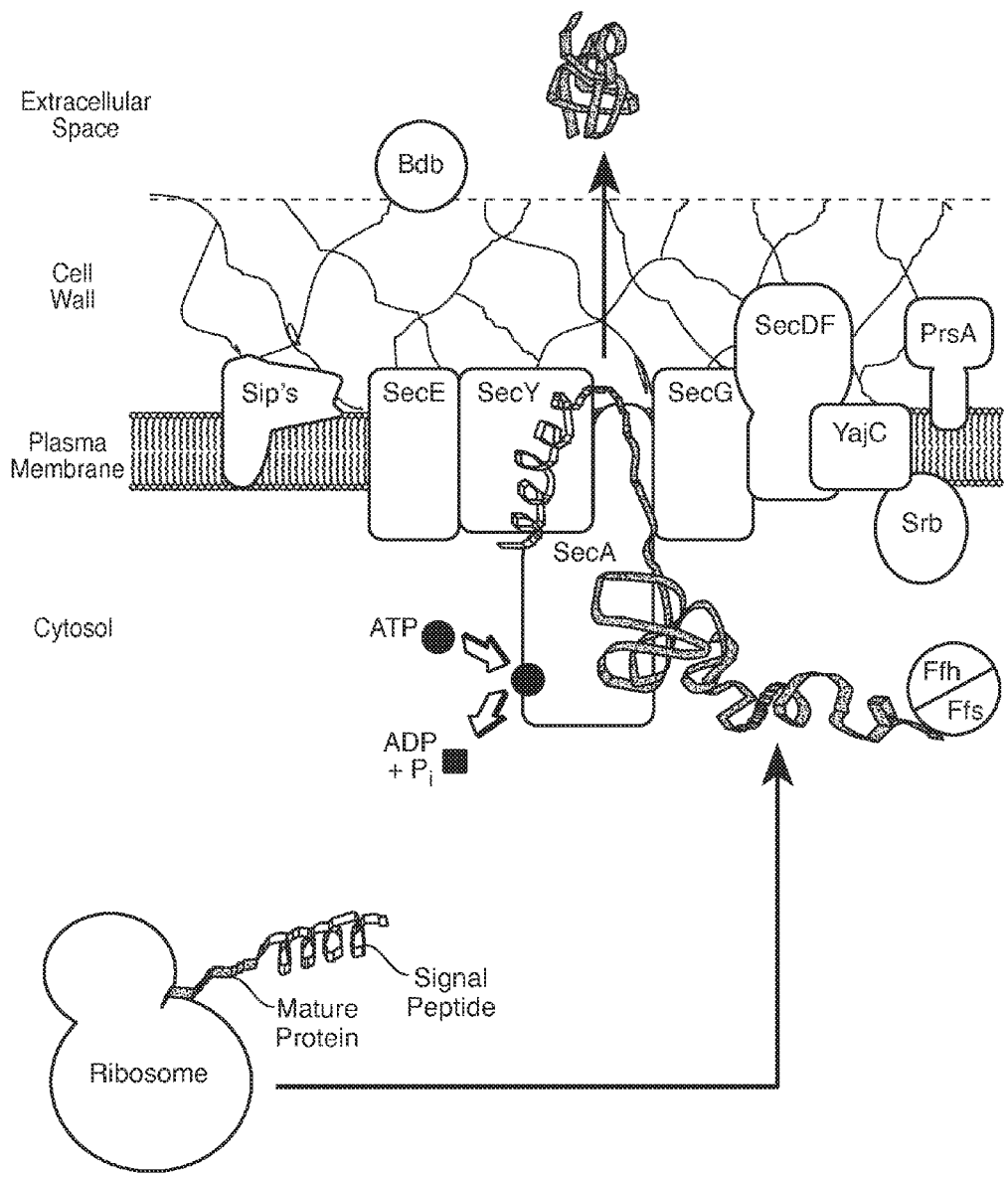

The transport of proteins via the bacterial plasma membrane is catalyzed via so-called Sec-translocase (FIG. 1). The latter consists of the integral membrane constituents SecY, SecE, SecG, SecD, SecF and YajC as well as the central component SecA that, as the so-called translocation ATPase, couples the energy of the ATP bond and hydrolysis to the translation of the polypeptide chain via the membrane [5, 6].

An efficient initiation of translocation of a secretory protein via the bacterial cytoplasm membrane requires the development of a functional complex consisting of at least the SecA protein, SecY and the export protein upon the membrane. As a consequence of these functional interactions as well as the exchange of ADP against ATP on the nucleotide bonding point 1 (NBS I) of SecA, a conformation change leads to a membrane insertion of SecA as well as the activation of the SecA ATPase activity and the initiation of translocation. The ATP hydrolysis on SecA is regulated by a double intramolecular mechanism. Investigations on *Escherichia coli* showed that in the free SecA, which is present cytosolically, the ATPase activity is down-regulated by the interactions of the regulatory elements IRA-1 and IRA-2 (intramolecular regulator of ATP hydrolysis) with NBS 1. It is assumed that the conformation change brought about on the basis of functional interactions between SecA and the export protein of SecA leads to a spatial removal of IRA-1 and IRA-2 from NBS 1, as a result of which, the SecA ATPase is activated [7,8]. During the secretory procurement of heterologous proteins with gram-positive bacteria, the translocation can represent a restrictive step on the basis of quality control or "proofreading activity" of the translocase. This control mechanism is necessary for the cell in order—with respect to its own proteins—to slot into the secretion path only those that are intended for export out of the cytosol. As for the heterologous proteins that are not adapted to the foreign export apparatus in an optimum fashion, this quality control, however, can represent an essential restrictive step. The ability of the heterologous expert proteins in terms of activating the translocation ATPase activity of the SecA protein is most likely decisive as to whether and with what efficiency a membrane transport of the heterologous export protein takes place or whether and to what extent there is a rejection of the heterologous export protein by the quality control of the Sec-translocase.

It is therefore the object of the invention to provide nucleotide sequences, protein sequences, bacteria as well as a method by means of which one can facilitate a secretory procurement of proteins that will be improved when compared to past known microbiological processes.

Using the invention-based nucleic acids as well as polypeptides, it is now possible to take proteins that so far were exported by the microorganisms only in small quantities or not at all and to obtain them in a secretory fashion with microorganisms or to make them with increased efficiency. Compared to the naturally occurring or gene-engineering unchanged nucleic acids, the invention-based nucleic acids code for a translocation ATPase, hereafter referred to as SecA, which causes or displays increased secretion for proteins. The term "increased secretion" is taken to mean a protein secretion that is increased when compared to the wild type of organisms or that is also possible for the first time. Furthermore, it is possible to provide microorganisms and methods by means of which one can facilitate a secretion and production of proteins with yields that are higher when compared to hitherto known microbial methods or that are possible for the first time.

Advantageous developments are given in the subclaims.

The object of the invention is a SecA protein (translocation ATPase) with an amino acid sequence, which, compared to the wild type SecA amino acid sequence, displays at least a change in the amino acid sequence or a modified form of these polypeptide sequences or isoforms, as a result of which, there is formed a SecA with increased secretion for proteins.

It was found quite surprisingly that a change (=exchange) of an amino acid of the amino acid sequence of the SecA protein will already lead to an increased secretion of proteins or to a secretion of proteins that will be possible for the first time. Several exchanged amino acids, for example, 2 to 7, however, can also bring about the increased secretion for proteins.

Changes in the area of the amino acid sequences that are responsible for the development of the regulatory elements IRA-1/IRA-2, or a modified form of these polypeptide sequences or isoforms thereof, turned out to be advantageous for the SecA with increased secretion for proteins, whereby in this case, the term "area" is intended to cover not only changes that are found precisely in the amino acid positions that are responsible for the development of the IRA-1/IRA-2 but also changes that, for example, are by 250 to 300 amino acids in front of or behind the particular amino acid positions for IRA-1 or IRA-2.

The positions of the invention-based changes in the amino acid sequence of SecA can be shifted within different microorganisms. For example, starting with the changes in the amino acid positions of SecA of *Staphylococcus carnosus*, one can also cover the changes in the amino acid sequence of the SecA of other microorganisms that correspond to these positions.

By means of a single change as well as by several changes in the area of the amino acid sequence that is responsible for the development of IRA-1 or IRA-2 as well as by combinations of changes in these areas, it was possible to obtain a SecA with increased secretion for proteins.

The invention-based polypeptides are distinguished by the following: They come from gram-positive or gram-negative bacteria, preferably from the family of the Bacillaceae, Staphylococcaceae, Enterobacteriaceae or Corynebacteriaceae, particularly preferably the genus *Bacillus, Staphylococcus, Escherichia* or *Corynebacterium*, particularly preferably the species of *Bacillus subtilis, Bacillus licheniformis, Bacillus amyloliquefaciens, Staphylococcus carnosus, Escherichia coli* or *Corynebacterium glutamicum*. Examples of bacterial in strain cultures that are obtainable from DSMZ (Deutsche Sammlung von Mikroorganismen and Zellkulturen GmbH/ German Collection of Microorganisms and Cell Cultures Co., Braunschweig) are, for example, *Bacillus subtilis* 168 or *Staphylococcus carnosus* TM 300. The invention at hand is characterized in greater detail by the listing of the previously mentioned bacteria strains, although this is not intended to be a restrictive list.

In the case of *Staphylococcus carnosus*, the amino acid sequences that form the IRA-1 in SecA extend to positions 721 to 772 and for IRA-2 to positions 448 to 567.

In the case of *Bacillus subtilis*, the amino acids sequences that form the IRA-1 in SecA extend to positions 716 to 767 and for IRA-2 to positions 442 to 561.

In the *Staphylococcus carnosus* that is isolated from SecA protein, it turned out to be advantageous to make at least one change in the area of the amino acids from position 198 to 772 or a modified form of these polypeptide sequences or isoforms thereof.

In the SecA protein isolated from *Bacillus subtilis*, it turned out to be advantageous to make at least one change in the area of the amino acids from position 442 to 767 or a modified form of these polypeptide sequences or isoforms thereof.

The object of the invention is a SecA with increased secretion for proteins or a part thereof containing an amino acid sequence according to SEQ ID No. 2, which displays at least one change in the group of the amino acids in position 198, 470, 474, 493, 537, 665 and/or 734 or a modified form of these polypeptide sequences or isoforms thereof.

Figure 2:
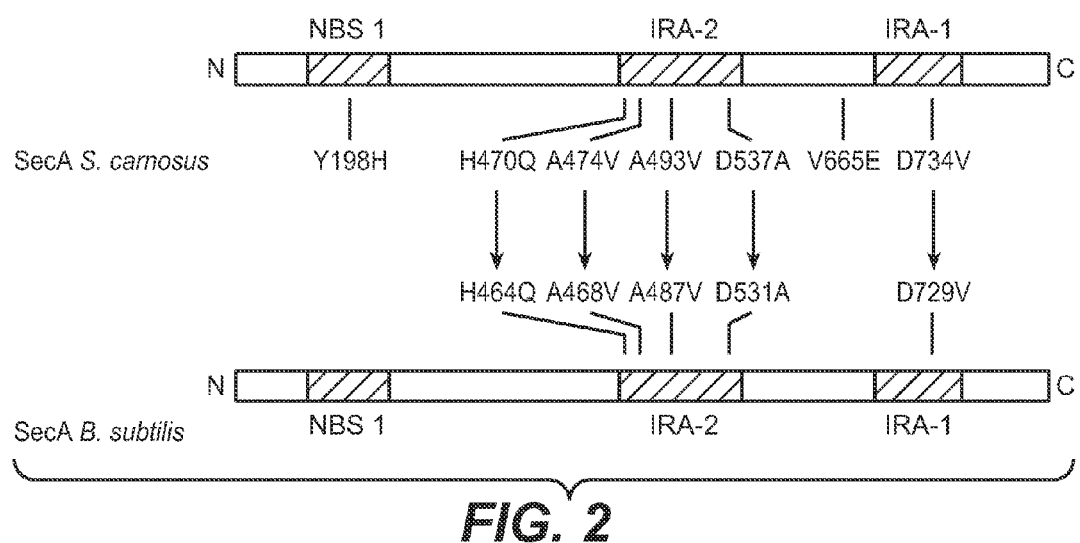

The following amino acid exchanges in the SecA of *Staphylococcus carnosus* provide to be successful by way of example (see FIG. 2):

Position 198: Tyrosine into histidine

Position 470: Histidine into glutamine

Position 474: Alanine into valine

Position 493: Alanine into valine

Position 537: Asparaginic acid into alanine

Position 665: Valine into glutamic acid

Position 734: Asparaginic acid into valine.

The invention at hand also relates to a SecA with increased secretion for proteins with an amino acid sequence according to SEQ ID No. 4, which displays at least one change from the group of amino acids in position 464, 468, 487, 531 and/or 729 or a modified form of these polypeptide sequences or isoforms thereof.

The following amino acid exchange in the SecA of *Bacillus subtilis* proved to be successful by way of example (see FIG. 2):

Position 464: Histidine into glutamine

Position 468: Alanine into valine

Position 487: Alanine into valine

Position 531: Asparaginic acid into alanine

Position 729: Asparaginic acid into valine

By isoforms, we mean proteins having the same or comparable action specificity, which, however, display a differing primary structure.

By modified forms according to the invention, we mean proteins where there are changes in the sequence, for example, on the C- or N-terminus of the polypeptide or in the area of conserved amino acids without, however, impairing the function of increased protein secretion. These changes can be made in the form of amino acid exchanges according to known methods.

The object of this invention includes polypeptides with the function of an SecA with increased secretion for proteins that are so altered in terms of their amino acid sequence that they can export homologous and/or heterologous proteins with increased activity out of the cells.

The object of this invention includes nucleic acids that code for a SecA with increased secretion of proteins containing a gene sequence secA, which in the secA gene, display at least one mutation or an allele, homologue or derivative of these nucleotide sequences or nucleotide sequences hybridizing with them.

It was now found quite surprisingly that already a mutation in a nucleotide of the secA gene leads to an increased secretion for proteins or to a secretion of proteins that would be possible for the first time. Several mutations, for example, 2 to 7, however, can also bring about the increased secretion of proteins.

At least one mutation in nucleotide areas that code for the regulatory elements IRA-1 and/or IRA-2 of the SecA proteins or an allele, homologue or derivative of these nucleotide sequences or nucleotide sequences hybridizing with them turned out to be advantageous for the expression of an SecA with increased secretion for proteins, where the term "area" is intended to cover not only mutations that lie precisely in the areas that code for IRA-1/IRA-2 but also mutations that, for example, are located 750 to 900 nucleotides before or after the areas that in each case code for IRA-1/IRA-2.

Both by means of a single mutation and by means of several mutations in the area of the nucleotide sequences that code for IRA-1 or IRA-2 as well as a combination of mutations in these areas, it was possible to bring about an increased export of proteins.

The invention-based nucleic acids are distinguished as follows: They are isolated from gram-positive or gram-negative bacteria such as, for example, from the family of Bacillaceae, Staphylococcaceae, Enterobacteriaceae or Corynebacteriaceae, preferably the genus of *Bacillus, Staphylococcus, Escherichia* or *Corynebacterium*, particularly preferably from *Bacillus subtilis, Bacillus licheniformis* or *Bacillus amyloliquefaciens, Staphylococcus carnosus, Escherichia coli* or *Corynebacterium glutamicum*. The invention at hand is characterized in greater detail by the listing of the above-mentioned bacteria strains, which, however, is not intended as a restrictive list.

In the case of *Staphylococcus carnosus*, the nucleotide area that codes for IRA-1 extends to the nucleotides from position 2161 to 2316 and for IRA-2 from position 1342 to 1701 (see also SEQ ID No. 1).

In the case of *Bacillus subtilis*, the nucleotide area that codes for IRA-1 extends to the nucleotides from position 2146 to 2301 and for IRA-2 from position 1324 to 1683 (see also SEQ ID No. 3).

In the case of the nucleic acids isolated from *Staphylococcus carnosus*, it turned out advantageous to have at least one mutation in the area of the nucleotides from position 592 to 2210 or an allele, homologue or derivative of these nucleotide sequences or nucleotide sequences hybridizing with them.

In the case of the nucleic acids isolated from *Bacillus subtilis*, it turned out advantageous to have at least one mutation in the area of the nucleotides from position 1392 to 2186 or an allele, homologue or derivative of these nucleotide sequences or nucleotide sequences hybridizing with them.

Particularly advantageous was found to be a nucleic acid containing a secA gene according to SEQ ID No. 1, which displayed at least one mutation in the gene from the group of the nucleotides in position 592, 1410, 1421, 1478, 1610, 1994 and/or 2210 or an allele, homologue or derivative of these nucleotide sequences or nucleotide sequences hybridizing with them.

The following mutations turned out to be successful in the secA gene of *Staphylococcus carnosus:*

Position 592: T to C

Position 1410: T to A

Position 1421: C to T

Position 1478: C to T

Position 1610: A to C

Position 1994: T to A

Position 2210: A to T.

Also particularly advantageous was found to be a nucleic acid containing a secA gene according to SEQ ID No. 3, which displayed at least one mutation from the group of the nucleotides in position 1392, 1403, 1404, 1460, 1461, 1592 and/or 2186 or an allele, homologue or derivative of these nucleotide sequences or nucleotide sequences hybridizing with them.

The following mutations turned out to be successful in the secA gene of *Bacillus subtilis:*

Position 1392: T to A

Position 1403: C to T

Position 1404: G to T

Position 1460: C to T

Position 1461: G to T

Position 1592: A to C

Position 2186: A to T.

In contrast to the mutations in positions 1392, 1592 and 2186, the two mutations of the nucleotides in position 1403 and 1404 or 1460 and 1461 on the protein level in each case lead to the exchange of only one amino acid.

Using the invention-based nucleic acid, one can efficiently export proteins out of the cells that in the presence of an unchanged SecA are exported only to a minor extent or not at all. The invention-based nucleic acids that code for a SecA with increased secretions for proteins bring about an altered control mechanism of the SecA for the proteins that are slotted out of the cell. In particular, heterologous proteins that are not adapted to the export apparatus of the host cell in an optimum fashion can now be particularly successfully exported with the help of the invention-based secA sequence. But the export of homologous proteins can also be advantageously improved with the help of the altered secA sequence.

By a nucleic acid or a nucleic acid fragment, we mean, according to the invention, a polymer consisting of RNA or DNA that can be single-strand or double-strand and that can contain optionally natural, chemically synthesized, modified or artificial nucleotides. The DNA polymer concept here also includes the genomic DNA, cDNA or mixtures thereof.

By alleles according to the invention, we mean equivalent nucleotide sequences that code for SecA proteins with increased secretion for proteins. Equivalent sequences are those sequences which, in spite of a deviating nucleotide sequence, for example, caused by the degeneration of the genetic code, will still code for the SecA protein with the desired increased secretion for proteins. Equivalent nucleotide sequences thus comprise naturally occurring variants of the sequences described herein as well as artificial nucleotide sequences that are obtained, for example, by chemical synthesis and that are possibly adapted to the codon custom of the host organism.

By equivalent nucleotide sequences, we also mean sequences with mutations, in particular, natural or artificial mutations of an originally isolated sequence that continue to code for a SecA protein with increased secretion for proteins. Mutations of the equivalents comprise substitutions, additions, deletions, exchanges or insertions of one or several nucleotide residues. This also includes so-called sense mutations that on the protein level can, for example, result in the exchange of conserved amino acids, which, however, do not lead to any basic change of the increased secretions of proteins of the invention-based SecA protein and thus are neutral in terms of function. That includes also changes of the nucleotide sequence that on the protein level relate to the C-terminus or N-terminus of a protein without, however, essentially impairing the function of the protein.

The invention at hand also covers those nucleotide sequences that one obtains by modification of the nucleotide sequence, resulting in corresponding derivatives. The objective of such a modification, for example, can be the further delimitation of the coding sequence contained therein or, for example, also the insertion of additional restriction enzyme interfaces.

The object of the invention at hand also includes artificial DNA sequences so long as they have the desired properties as described above. Such artificial DNA sequences can, for example, be determined by the re-translation of amino acid sequences by means of computer assisted programs. Particularly suitable are coding DNA sequences that were obtained by re-translation of a polypeptide sequence according to the codon use that is specific for the host organism. The specific codon utilization can easily be determined by an expert who is familiar with molecular genetic methods by computer analysis of other already known genes of the organism that is to be transformed.

By homologous sequences according to the invention, we mean those that are complementary for the invention-based nucleotide sequences and/or that hybridize with them. The "hybridizing sequences" concept according to the invention includes substantially similar nucleotide sequences from the group of DNA or RNA that, under known stringent conditions, enter into a specific interrelationship (bonding) with the previously mentioned nucleotide sequences. That includes also short nucleotide sequences with a length of, for example, 10 to 30, preferably 12 to 15 nucleotides. According to the invention, this, among other things, also covers so-called primers or probes.

According to the invention, that also includes the sequence areas that precede (structural genes) (5'- or upstream) and/or follow (3'- or downstream) the coding areas. This especially includes sequence areas with regulatory function. They can influence the transcription, the RNA stability or the RNA processing as well as the translation. Examples of regulatory sequences, among other things, are promoters, enhancers, operators, terminators, translation amplifiers or ribosome bonding points.

Basically, genes can be amplified and subsequently isolated by known methods such as, for example, the polymerase chain reaction (PCR) with the help of short synthetic nucleotide sequences (primers). The primers used are generally produced on the basis of known gene sequences resting on existing homologies in conserved areas of the genes and/or considering the GC content of the DNA of the microorganism that is to be investigated.

Another procedure for the isolation of coding nucleotide sequences is the complementation of so-called defect mutants that, at least in phenotypical terms, display a function loss in the activity of the gene to be investigated or of the corresponding protein. By "complementation," we mean the elimination of the gene defect of the mutant and extensive restoration of the original phenotype prior to mutagenesis, which is attained by the introduction of functional genes or gene fragments.

A conventional mutagenesis method for the production of defect mutants, for example, is the treatment of the bacterial cells with chemicals such as, for example, N-methyl-N-nitro-N-nitrosoguanidine or UV radiation. Such methods for triggering mutation are generally known and, among other things, can be followed up in Miller (*A Short Course in Bacterial Genetics, A Laboratory Manual and Handbook for Escherichia coli and Related Bacteria* (Cold Spring Harbor Laboratory Press, 1992)) or in the handbook "*Manual of Methods for General Bacteriology*" by the American Society for Bacteriology (Washington D.C., USA, 1981).

The object of the invention furthermore includes a gene structure containing at least one of the previously described nucleotide sequences that code for a SecA with increased secretion for proteins as well regulatory sequences that are tied in with them in operational terms, which control the expression of the coding sequences in the host cell. Corresponding gene structures, for example, can be chromosomes, plasmids, vectors, phages or other nucleotide sequences that are not closed in a circular manner.

The invention at hand relates to a vector containing a nucleotide sequence of the kind described previously and coding for a SecA with increased secretion for proteins, regulative nucleotide sequences that are operationally tied in with it as well as additional nucleotide sequences for the selection of transformed host cells, for replication within the host cell or for integration into the corresponding host cell genome.

Figure 5:
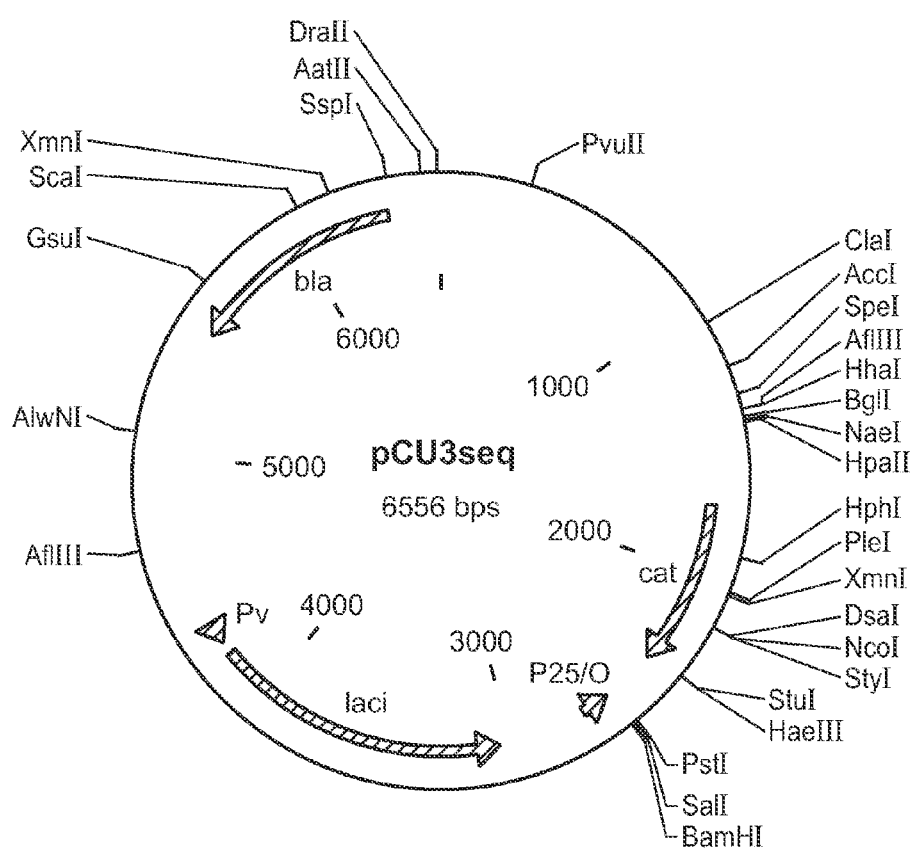
Figure 6:
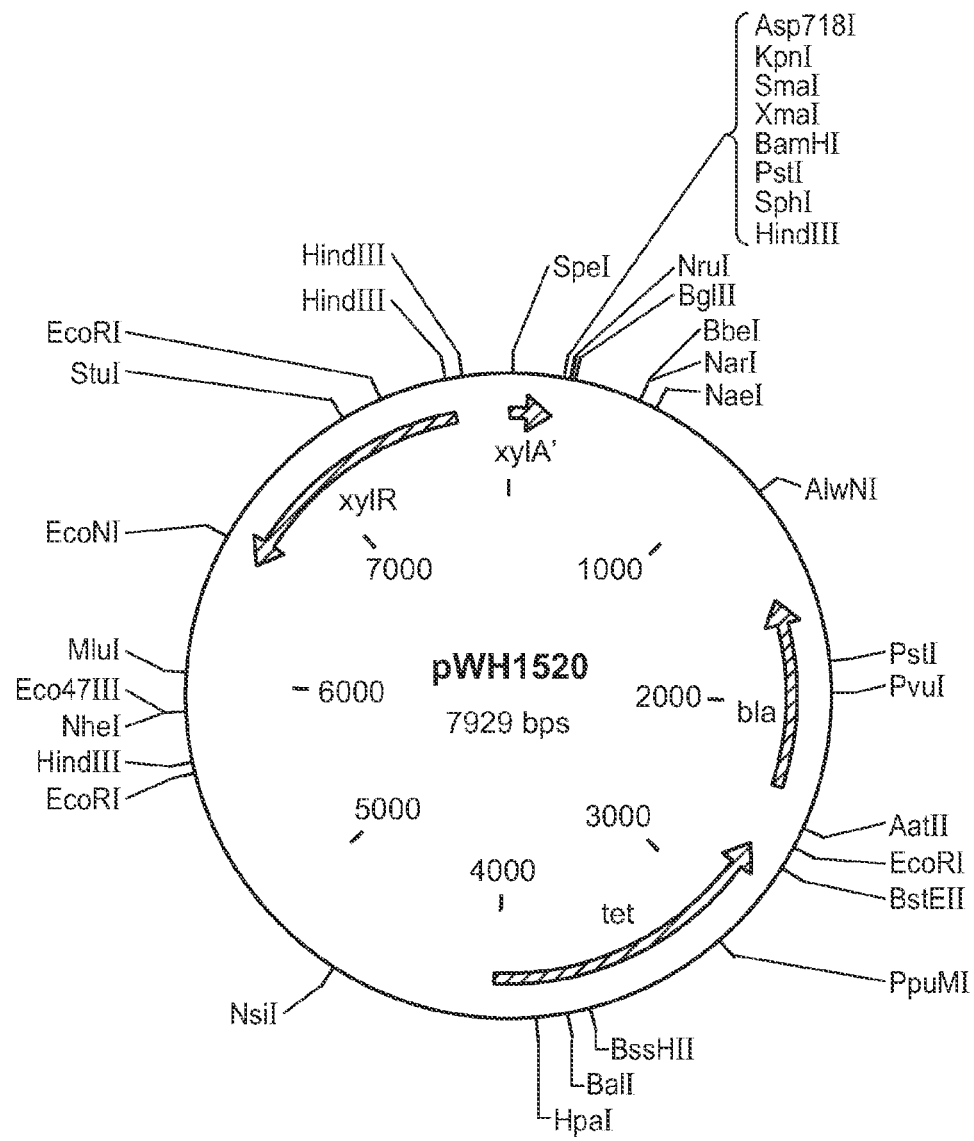
Figure 7:
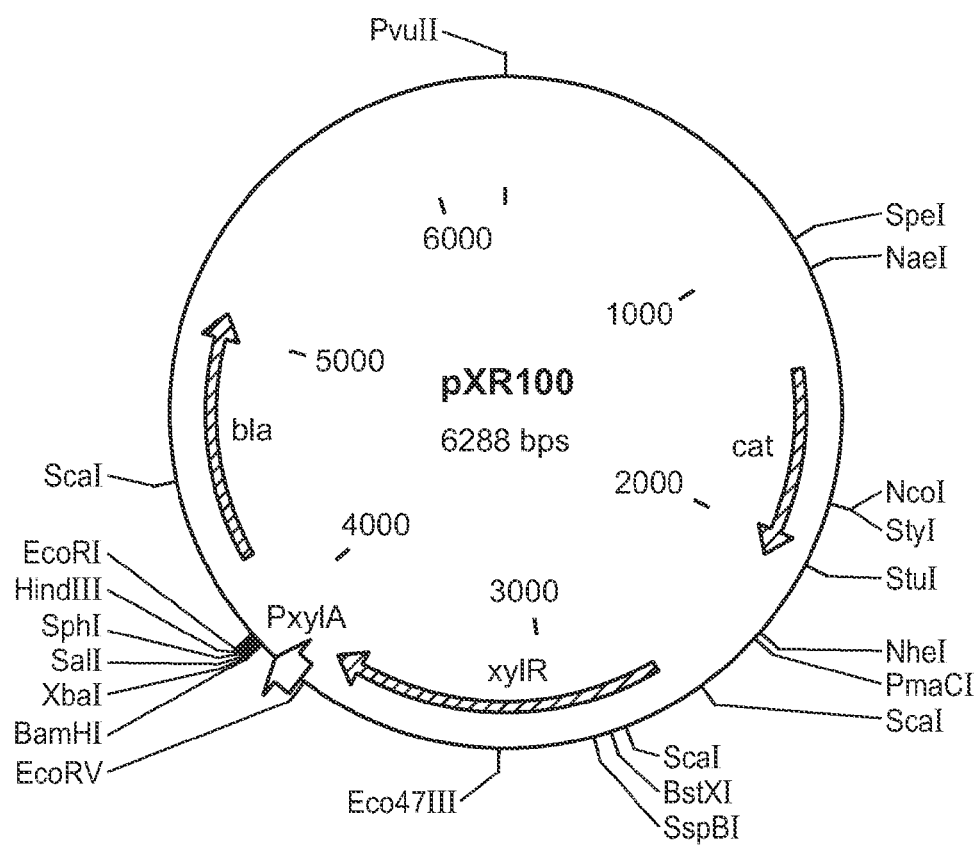

Suitable as vectors are those that are replicated in bacteria such as, for example, pWE1520 [17], pCU3 or pXR100 (see also FIG. 5, 6 or 7). Other plasmid vectors can be used in a similar manner. This listing, however is not intended to be restrictive as regards the invention at hand.

Using the invention-based nucleic acid sequences, one can synthesize corresponding probes or also primers, and one can use them for amplifying and isolating preferably gram-positive bacterial, for example, with the help of genes from other microorganisms that are analogous to the PCR technique. The object of the invention at hand thus also includes a probe for the identification and/or isolation of genes coding for proteins that participate in the export of proteins, whereby this probe is made starting with the invention-based nucleic acid sequences of the kind described earlier and contains a marking suitable for detection. The probe can be a segment out of the invention-based sequence, for example, out of a conserved area, which, for example, has a length of 10 to 30 or preferably 12 to 15 nucleotides and which can hybridize under stringent conditions specifically with homologous nucleotide sequences. Numerous suitable markings are known from the literature on the subject. Instructions for this purpose can be found by the expert, among other things, for example, in the handbook by Gait: Oligonucleotide Synthesis: A Practical Approach (IRL Press, Oxford, UK, 1984) and by Newton and Graham: PCR (Spektrum Akademischer Verlag/Publishers, Heidelberg, Germany, 1994) or, for example, in the handbook: "*The DIG System Users Guide for Filter Hybridization*" by Firma Roche Diagnostics/the Roche Diagnostics Company (Mannheim, Germany) and by Liebl et al. (*International Journal of Systematic Bacteriology* (1991) 41: 255-260).

The object of the invention at hand furthermore includes the transfer of at least one of the invention-based nucleic acid sequences or a part thereof coding for a SecA with increased secretion for proteins, an allele, homologue or derivative thereof into a host system. That also includes the transfer of an invention-based gene structure into a host system. This transfer of DNA into a host cell is accomplished according to gene engineering methods. As a preferred method, one might mention here the transformation and, especially in a preferred manner, the transfer of DNA by electroporation. Gram-positive host organisms proved to be particularly suitable. A transformed microorganism, resulting from a successfully performed nucleic acid transfer, will differ from the correspondingly non-transformed microorganism in that it contains nucleic acids of the kind according to the invention and can bring them to expression accordingly. As representative of a suitable host system, we might mention organisms of the genus of *Bacillus* or *Staphylococcus* and preferably the species of *Bacillus subtilis, Bacillus licheniformis, Bacillus amyloliquefaciens* or *Staphylococcus carnosus*. As culture medium, depending on the requirements, we find usable a complex medium such as, for example, LB Medium (T. Maniatis, E. F. Fritsch and J. Sambrook, *Molecular Clonin [sic]: A Laboratory Manual*, Cold Spring Harbor Laboratory, Cold Spring Harbor, N.Y., 1989)) or also a mineral salt medium such as, for example, CGXII medium (Keilhauer, C. et al., 1993, J. Bacteriol., 175: 5593-5603). After corresponding cultivation, the bacteria suspension can be harvested and can be used for further examination, for example, for transformation or isolation of nucleic acids according to currently customary methods. This procedure can analogously be applied also to other gram-positive or gram-negative bacteria strains. Bacteria of the family of *Bacillus* or *Staphylococcus* are preferred here as host systems. In a particularly preferred manner, one might mention here the species *Bacillus subtilis, Bacillus licheniformis, Bacillus amyloliquefaciens* or *Staphylococcus carnosus*.

Moreover, the invention at hand also includes bacteria strains as host systems that are distinguished as mutated or wild type strains suitable for protein production because their metabolism flow runs increasingly in the direction of a biosynthesis of proteins. Suitable according to the invention are also those microorganisms that are known to the expert from microbial production methods such as, for example, Enterobacteriaceae or Corynebacteriaceae.

As host organisms, one can also use microorganisms where one or several gene(s), coding for proteins, components or factors that are responsible for the transport of proteins through the bacterial plasma membrane, are so altered that, in addition to the invention-based SecA protein, they contribute to an increased transport of proteins through the plasma membrane. That, for example, could be the other known constituents (secY, secE, secG, secD, secF and yajC) of Sec-translocase. By way of example, we might mention here the host organisms of the family of *Bacillus* or *Staphylococcus*.

The invention at hand will be explained in greater detail by means of the selected examples referring to microorganisms, although it is in no way restricted by them.

The invention at hand furthermore relates to a genetically altered microorganism, containing in a replicable form an invention-based nucleic acid of the kind previously described.

The invention also comprises a genetically altered microorganism, containing in replicable form a gene structure or a vector of the kind previously described.

The object of the invention furthermore also includes a genetically altered microorganism, containing an invention-based polypeptide with the function of an increased secretion for proteins when compared to the microorganism that is accordingly not altered in genetic terms. An invention-based genetically altered microorganism is furthermore distinguished by the following: It is a gram-positive or gram-negative bacterium such as, for example, an organism from the family of the Bacillaceae, Staphylococcaceae, Enterobacteriaceae or Corynebacteriaceae, particularly preferably the genus of *Bacillus* or *Staphylococcus*. Particularly preferred, for example, are *Bacillus subtilis, Bacillus licheniformis, Bacillus amyloliquefaciens* or *Staphylococcus carnosus*.

The invention at hand furthermore relates to a method for the microbial production of proteins where at least one of the invention-based nucleic acids isolated from a gram-positive or gram-negative bacterium is transferred into a host organism or is generated there with the means known to the expert and is expressed there, where this genetically altered microorganism is employed for the microbial production of proteins and where the correspondingly formed protein is isolated out of the culture medium.

The genetically altered microorganism, made according to the invention, can be cultivated continuously or discontinuously by way of the batch method (set cultivation) or by the fed batch (feed method) or repeated fed batch methods (repetitive feed method) for the purpose of producing proteins. A summary of known cultivation methods can be found in the textbook by Chmiel (Bioprozesstechnik 1. Einfuehrung in die Bioverfahrenstechnik—Bioprocess technique 1. Introduction into Bioprocess Technique (Gustav Fischer Verlag/Publishers, Stuttgart, 1991)) or in the textbook by Storhas (Bioreaktoren und periphere Einrichtungen—Bioreactors and Peripheral Devices (Vieweg Verlag/Publishers, Braunschweig/Wiesbaden, 1994)).

The culture medium to be used for this purpose must suitably meet the requirements of the particular strains. Description of culture media of various microorganisms can be found in the handbook "*Manual of Methods for General Bacteriology*" of the American Society of Bacteriology (Washington D.C., USA, 1981). As a source of carbon, one might use sugars and carbohydrates such as, for example, glucose, saccharose, lactose, fructose, maltose, molases, starch and cellulose, oils and fats such as, for example, soybean oil, sunflower oil, peanut oil and coconut fat, fatty acids such as, for example, palmitinic acid, stearic acid and linoleic acid, alcohols such as, for example, glycerin and ethanol, and organic acids such as, for example, acetic acid. These substances can be used individually or as a mixture. As nitrogen source, one can employ organic nitrogen-containing compounds such as peptones, yeast extract, meat extract, malt extract, corn spring water, soybean flower and urea, or inorganic compounds such as ammonium sulfate, ammonium chloride, ammonium phosphate, ammonium carbonate and ammonium nitrate. The nitrogen sources can be used individually or as a mixture. As a phosphorus source, one can employ phosphoric acid, potassium dihydrogen phosphate or dipotassium hydrogen phosphate or the corresponding sodium-containing salts. The culture medium furthermore must contain metal salts such as, for example, magnesium sulfate or iron sulfate that are necessary for growth. Finally, one can employ essential growth substances such as amino acids and vitamins in addition to the abovementioned substances. Suitable preliminary stages can, moreover, be added to the culture medium. The substances to be used and listed can be added to the culture in the form of a one-time preparation or they can be fed-in suitably throughout cultivation.

To check the pH control of the culture, one can suitably employ basic compounds such as sodium hydroxide, potassium hydroxide, ammonia or ammonia water or acid compounds such as phosphoric acid or sulfuric acid. To check the foam development, one can employ anti-foaming agents such as, for example, fatty acid polyglycol esters. To maintain the stability of plasmids, one can add suitable selectively acting substances to the medium, for example, antibiotics. To maintain aerobic conditions, one introduces oxygen or oxygen-containing gas mixtures into the culture such as, for example, air. The temperature of the culture normally is between 30° C. and 38° C., and preferably it is 37° C. The culture is continued until a maximum of the desired protein has been formed. This objective is normally attained within 8 to 72 hours.

The proteins can be analyzed by activity determination, sequencing or electrophoresis.

The microorganisms that are the object of the invention at hand can, for example, make proteins from glucose, saccharose, lactose, mannose, fructose, maltose, molasses, starch, cellulose or from glycerin and ethanol. This may involve the already previously more thoroughly described representatives of the gram-positive or gram-negative bacteria. The microorganisms that are genetically altered according to the invention here are distinguished by increased protein secretion when compared to the correspondingly unchanged microorganisms (wild type) or the microorganisms that merely contain the vector without the gene insert. In a particular embodiment of the invention at hand, it is shown that the expression of the invention-based secA gene in the homologous *Bacillus subtilis* system (that is to say, all components of the Sec transport apparatus come from *Bacillus subtilis*) will result in an at least triple increase in protein accumulation in the medium when compared to the control strains. By overexpression of additional genes that have a positive effect upon the general metabolism of protein biosynthesis, one can expect an additional increase in protein production.

Using the invention-based method, one can make pharmaproteins, hormones, enzymes, growth factors or, for example, cytokines. In that way, for example, one can make proteases, amylases, carbohydrases, lipases, epimerases, tautomerases, mutases, transferases, kinases or phosphatases in a microbial manner.

By way of example, the figures show plasmids, a schematic overview of the Sec protein secretion apparatus, a representation of the SecA proteins with the invention-based mutations as well as an experimental evidence of the increased protein secretion using the invention-based nucleic acids.

The following are shown:

FIG. 1:

Sec-Protein Secretion Apparatus of Gram-Positive Bacteria

FIG. 2:

Diagram illustrating the SecA Proteins of *S. carnosus* and *B. subtilis*. Shown in the drawing are the suppressing mutations of *S. carnosus* SecA, which are obtained by means of selection. The mutations marked by arrows were transferred by specifically directed mutagenesis individually to the corresponding amino acid positions from the plasmid-coded *B. subtilis* SecA.

FIG. 3:

Evidence of PhoB or PhoB L15Q by Means of Western Blot in Cell Extracts and Culture Supernatants of *Bacillus subtilis* DB 104 Strain in Case of Co-Expression of Plasmid-Coded PhoB or PhoB L15Q and Mutated SecA Proteins. The induction of the PhoB expression was accomplished with 0.5 mM IPTG, the SecA expression was induced with 0.2% xylose. p: PhoB L15Q precursor; m: Mature PhoB (significantly increased quantities are indicated with the arrow); L15Q: Variant of alkaline phosphatase PhoB, which, on the basis of an amino acid exchange of leucine into glutamine on position 15 in the signal sequence, is exported only very inefficiently in the unaltered *Bacillus subtilis*; pWA−secA: Empty vector; pWA+secA: Vector with wild type SecA; pWAX: Plasmid with invention-based mutation of the secA of *Bacillus subtilis*, X stands for one of the mutations in position 464, 468, 487, 531 or 729.

| Trace | Experimental Preparation |
|---|---|
| 1 | Cell extract; plasmid pWA − secA; PhoB unchanged |
| 2 | Supernatant; plasmid pWA − secA; PhoB unchanged |
| 3 | Cell extract; plasmid pWA − secA; L15Q |
| 4 | Supernatant; plasmid pWA − secA; L15Q |
| 5 | Cell extract; plasmid pWA + secA; PhoB unchanged |
| 6 | Supernatant; plasmid pWA + secA; PhoB unchanged |
| 7 | Cell extract; plasmid pWA + secA; L15Q |
| 8 | Supernatant; plasmid pWA + secA; L15Q |
| 9 | Cell extract; plasmid pWA464; L15Q |
| 10 | Supernatant; plasmid pWA464; L15Q |
| 11 | Cell extract; plasmid pWA468; L15Q |
| 12 | Supernatant; plasmid PWA468; L15Q |
| 13 | Cell extract; plasmid pWA487; L15Q |
| 14 | Supernatant; plasmid pWA487; L15Q |
| 15 | Cell extract; plasmid pWA531; L15Q |
| 16 | Supernatant; plasmid pWA531; L15Q |
| 17 | Cell extract; plasmid pWA729; L15Q |
| 18 | Supernatant; plasmid pWA729; L15Q |

FIG. 4:

| Plasmid Vector pDEL6; | |
|---|---|
| SecAS.c.: | secA gene of *Staphylococcus carnosus*; |
| cat: | Chloramphenicol resistance gene; |
| orf1 and orf3: | Areas that are located in the chromosome of *Bacillus subtilis* before (orf1) or behind (orf3) the secA gene. These areas are used for exchanging the secA gene in the chromosome of *Bacillus subtilis* against the secA gene of *Staphylococcus carnosus*. |
| bla: | Gene sequence coding for β-lactamase. |

FIG. 5:

| Plasmid Vector pCU3seq; (corresponding to the pEF1 plasmid from publication [19]) | |
|---|---|
| cat: | chloramphenicol resistance gene |
| P25/O: | bacteriophages T5 promoter $PN_{25}$/lac operator |
| lacI: | gene coding for lac repressor |
| Pv: | *B. subtilis* vegII promoter |
| bla: | β-lactamase. |

FIG. 6:

| Plasmid Vector pWH1520 | |
|---|---|
| bla: | β-lactamase |
| tet: | tetracycline resistance gene |
| xylR: | repressor gene of the xylose operon from *Bacillus megaterium* |
| xylA: | N-terminal fragment of xylose isomerase under the control of a xylose-inducible promoter. |

FIG. 7:

| Plasmid Vector pXR100; | |
|---|---|
| bla: | β-lactamase |
| xylR: | repressor gene of the xylose operon from *Bacillus megaterium* |
| PxylA: | xylose-inducible promoter of xylose isomerase |
| cat: | chloramphenicol resistance gene. |

EXEMPLARY EMBODIMENTS

General Description

First of all, a *Bacillus subtilis* strain was constructed with an artificially increased quality control of the SecA protein (hereafter called RMA=replacement mutant SecA).

The strain was generated in that the *Bacillus subtilis* secA gene, lying on the chromosome, was exchanged against the secA gene of *Staphylococcus carnosus*. This exchange resulted in an artificially increased quality control of Sec-translocase. The heterologous protein OmpA from *E. coli* was used as a model protein. The artificially increased quality control of the SecA protein meant that the heterologous protein OmpA of *E. coli* was specifically excluded from export. Moreover, the RMA displayed a cold-sensitive growth (that is to say, no growth at 25° C.) as well as defects in the formation of spores and the development of natural competence.

In the following, suppressor mutants of the RMA were selected, which again can grow at 25° C. and/or which again have the ability for the formation of spores. The characterization of these suppressor mutants meant that in these mutants, changes had occurred in the foreign secA gene. The corresponding amino acid changes related above all to the two areas IRA-1 and IRA-2 that are involved in the regulation of ATP hydrolysis on the NBS-1 of SecA. The further characterization of the suppressor mutants, moreover, showed that the heterologous OmpA protein, which is almost completely excluded from export in the RMA, can be exported in a definitely better manner in the suppressor mutants. On the basis of comparisons with *Escherichia coli* SecA mutants from bibliography data [10], which partly were identical to the invention-based mutations in the secA gene or the invention-based changes in the amino acid sequence of the SecA protein on the corresponding positions, one may assume that the mutations, identified in the IRA elements of *Staphylococcus carnosus* SecA, weakened the repression of ATP hydrolysis on the NBS-1 in SecA, as a result of which, the basal ATPase activity was increased [9, 10]. The altered *Staphylococcus carnosus* SecA variants thus represent SecA proteins that permit a better export of normally inefficient or not at all exported heterologous proteins.

All of the RMA and the isolated suppressor mutants still have the foreign secA gene of *Staphylococcus carnosus* and thus still represent an artificial situation with a mixed Sec-translocase; therefore, in the following, the discovered changes (individually and also in combination) were transferred to the homologous *Bacillus subtilis* SecA. The co-expression of the mutated *Bacillus subtilis* SecA proteins with various inefficiently transported export proteins in *Bacillus subtilis* showed that also in the now homologous system (that is to say, all components of the Sec transport apparatus come from *B. subtilis*), one could observe an improved export of the examined proteins (shown in FIG. 3 using the example of an inefficiently exported variant of the alkaline phosphatase PhoB of *B. subtilis*).

1. Construction of the *Bacillus subtilis* SecA Exchange Mutant (RMA)

The pDEL6 plasmid, which was used for the construction of the RMA, was constructed as follows:

A pOrf3 plasmid was obtained by ligation of a 0.5 kb Asp718/Pst1 fragment of plasmid pMKL4 [11] into the plasmid pGEM3Z (Promega). A 2.4 kb NsiI/Pst1 fragment of plasmid pBO1 [12] was ligated into the pOrf3 plasmid, which was digested with Pst1. The secA gene of the resultant plasmid pDEL1 was exchanged by digestion with SpeI and SalI against a 1.4 kb EcoR1/SalI fragment of pDG268 plasmid [13], which carries the gene for chloramphenicol acetyl transferase (cat) from which resulted the plasmid pDEL3. Subsequently, various secA gene were ligated into the plasmid pDEL3, which was digested with SalI and Pst1. The pDEL5 plasmid carries the *B. subtilis* secA gene, which was obtained by SalI/Pst1 digestion from pMKL4 plasmid [11] as 2.5 kb fragment. The pDEL6 plasmid carries the *S. carnosus* secA gene, which was obtained by SacI/Pst1 digestion from pMA12 plasmid [14] as 2.6 kb fragment. The pDEL6 fragment, which was used for the construction of the RMA, thus contains areas from five different plasmids:

secA gene from plasmid pMA12
chloramphenicol resistance gene (cat) from plasmid pDG268
orf1 from plasmid pBO4
orf3 from plasmid pMKL4
residual area (lacZ and bla) from plasmid pGEM3Z.

The *bacillus subtilis* SecA exchange mutant (RMA) was obtained in that the wild type strain *B. subtitles* DB104 (his, nprR2, nprE18, ΔaprA3) [15] was transformed with the linearized plasmid pDEL6 and that clones were selected, which were able to grow in the presence of 10 μg/ml of chloramphenicol. The secA gene exchange was verified by Southern Blot analyses, whereby the *B. subtilis* or *S. carnosus* secA gene was used as probe.

2. Isolation of Suppressor Mutants of *B. subtilis* RMA

The *B. subtilis* RMA was used as parental strain in order to isolate suppressor mutants that again can grow at 25° C. or that can sporulate better than the RMA.

To isolate the cold-resistant suppressor mutants of the RMA, Lurai-Bertani (LB) medium was inoculated after addition of 10 μg/ml of chloramphenicol with $10^6$ cells of RMA and was incubated for 48 hours at 25° C. Between 100 and 1,000 cells were plated out on LB agar plates and were incubated for another 24 hours at 25° C. As an alternative, $10^6$ cells from a culture of RMA that was incubated overnight at 37° C. were plated out directly on LB agar plates and were incubated for 24 hours at 25° C. The stability of the mutation of the resultant suppressor mutants was examined in that the mutants, after inoculation and incubation at 37° C., also after renewed inoculation and incubation at 25° C., displayed additional growth.

To isolate suppressor mutants, which again can sporulate better than RMA, 5 ml of sporulation medium [16] 1:100 were inoculated with a washed overnight solution of RMA and were incubated for at least 24 hours at 37° C. 100 μl of the preparation was heated for 30 minutes at 80° C. after the addition of the same quantity of chloroform. The spores were plated out on LB agar plates and were incubated for 2 days at 25° C. Mutants that were able to grow under these selection conditions were isolated.

3. Cloning and Sequencing of the secA Gene of the Suppressor Mutants

*B. subtilis* DB 104 was used in order to differentiate whether the suppressing mutations of the suppressor mutants are located in the secA gene of *S. carnosus* or another gene of *B. subtilis*. For this purpose, *B. subtilis* DB 104 was transformed with chromosomal DNA of the suppressor mutants and the chloramphenicol-resistant clone was selected. The resultant transformants were tested to determine whether they can also grow at 25° C., in other words, they also had integrated into the chromosome, in addition to the gene for chloramphenicol acetyl transferase, the neighboring, downstream-located *S. carnosus* secA gene with the suppressing mutation instead of the *B. subtilis* secA gene. It was found that the suppressing mutations of the suppressor mutants are located in the secA gene of *S. carnosus*. Therefore, a cloning of the secA gene was subsequently performed.

In order to clone the *S. carnosus* secA gene of the suppressor mutants under the control of the xylose-inducible promoter xylA, an amplification was performed of secA by means of PCR using chromosomal DNA of the suppressor mutants as matrices. The following primers were used for this purpose:

SecAS.c.NBamH1 (5' CGGGATCCCAAAGGAGCGAA-CAGAATGGG 3') (SEQ ID NO:5)

SecAS.c.CSph1 (5' ACATGCATGCATACAACTTACTATT-TACCGCAGC 3') (SEQ ID NO:6) (underlined bases indicate the BamH1 or Sph1 interfaces). After amplification, a 2.56 kb fragment was obtained, which was digested with BamH1 and Sph1 and which was ligated into the likewise BamH1/Sph1 digested vector pWH1520 [17], as a result of which, the plasmid pWHsecAS.c.$_{Supp.}$ were obtained. The sequencing of the secA genes was performed with IRD800 marked primers:

SecAS.c.H1 (5' AACTGCAACGATGCCGAC 3'; SEQ ID NO:7),

SecAS.c.H2 (5' GTGCTGATAAAGCTGAACG 3'; SEQ ID NO:8),

SecA S.c.H3 (5' AATTCCAACGAACCGTCC 3'; SEQ ID NO:10),

SecAs.c.H4 (5' GACAAGGTGACCGCGGAG 3'; SEQ ID NO:9),

SecAS.c.H5 (5' AAGGTAAAGATCGTGAGG 3'; SEQ ID NO:11) and

SecAs.c.R5 (5' CTGTTCAAGTTCAATCCG 3'; SEQ ID NO: 12) (MWG) using the Thermo Sequenase Fluorescent Labeled Primer Cycling Sequencing Kit (Amersham Pharmacia Biotech) as specified by the manufacturer.

4. Transfer of Suppressing Mutations into the SecA of *B. subtilis*

The transfer of suppressing mutations in the SecA of *S. carnosus* upon the corresponding amino acid residues in the *B. subtilis* was performed by means of specifically targeted mutagenesis of plasmid-coded *B. subtilis* SecA using Quick-Change Site-Directed Mutagenesis Kit by Stratagene according to data provided by the manufacturers. As matrix for the PCR reaction, we used the plasmid pMKL40 and the following primer pairs for insertion of the desired mutations (the altered bases are underlined):

1. Exchange of histidine to glutamine on amino acid position 464

5' GTGTTAAATGCCAAAAACCAAGAACGT-GAAGCGCAGATC 3' (SEQ ID NO:13)

5' GATCTGCGCTTCACGTTCTTGGTTTTTG-GCATTTAACAC 3' (SEQ ID NO:14)

2. Exchange of alanine to valine on position 468

5' CCATGAACGTGAAGTTCAGATCATTGAA-GAGGCCGGCC 3' (SEQ ID NO:15)

5' GGCCGGCCTCTTCAATGATCTGAACT-TCACGTTCATGG 3' (SEQ ID NO:16)

3. Exchange of alanine to valine on position 487

5' CGATTGCGACTAACATGGTTGGGCGCGGAACGG 3' (SEQ ID NO:17)

5' CCGTTCCGCGCCCAACCATGTTAGTCGCAATCG 3' (SEQ ID NO:18)

4. Exchange of asparaginic acid to alanine on position 531

5' CCGGACGTCAGGGAGCCCCGGGGATTACTC 3' (SEQ ID NO:19)

5' GAGTAATCCCCGGGGCTCCCTGACGTCCGG 3' (SEQ ID NO:20)

5. Exchange of asparaginic acid to valine on position 729

5' GGATGGATCATATTGTTGCGATGGAT-CAGCTCCGCCAAGGG 3' (SEQ ID NO:21)

5' CCCTTGGCGGAGCTGATCCATCGCAA-CAATATGATCCATCC 3' (SEQ ID NO:22)

A 1.86 kb SnaB1/Sph1 secA fragment from pMKL40 in which the desired mutation was present was subsequently ligated with the 8.67 kb fragment of the mWMKL1 vector that was digested with SnaB1 and Sph1. From this resulted the plasmid pWAX (X here stands for one of the constructs 464, 468, 487, 531 or 729), which contained the secA genes with the desired mutations in a *B. subtilis* expression vector under the control of the xylose-inducible promoter pxylA. The sequencing of the altered *B. subtilis* secA genes was performed with the following primers:

SecAB.s.H1 (5' GTACAGCTAAGACAGAGG 3'; SEQ ID NO:23),

SecAB.s.H2 (5' TTGACCGCTTCGGCATGG 3'; SEQ ID NO:24),

SecAB.s.H3 (5' AAGGGATTCACCTTCGTGC 3'; SEQ ID NO:25),

SecAB.s.R1 (5' TTTCCTTCCATCGTGCGG 3'; SEQ ID NO:26),

SecAB.s.R2 (5' TTCAGTAAGCTGTACAGC 3'; SEQ ID NO:27) and

SecAB.s.R3 (5' TTTCCGTC ATGAAGCGCC 3'; SEQ ID NO:28).

The expression of the SecA proteins was checked out in that LB medium was inoculated at an $OD_{600}$ of 0.4 after addition of 0.2% (w/v) xylose with the strains *B. subtilis* DB104, which contained the plasmid pWAx and were then incubated for 4 hours at 37° C. Cells from 2 ml of culture were centrifuged off and were boiled up after solution with 50 µl of lysis buffer (10 mM Tris/HCl, pH 8.0, 25 mM $MgCl_2$, 200 mM NaCl, 5 mg/ml lysozyme) in the same volume of 2× Laemmli sample buffer. The proteins were separated in a 10% SDS polyacrylamide gel and the SecA was documented by means of Western Blot analysis using *B. subtilis* SecA-specific antibodies. The functional mode of the altered *B. subtilis* SecA proteins was checked in that the temperature-sensitive *B. subtilis* secA mutant NIG1152 (met, his, div341[fs]) [18] was transformed with the pWAX plasmids and the growth defect of the mutant was complemented at the nonpermissive temperature of 42° C. by induction of the SecA expression with 0.2% (w/v) xylose.

5. Study of Protein Export of an Alkaline Phosphatase PhoB

A study was made to determine as to whether protein export in *B. subtilis* wild type is improved by expression of the altered *B. subtilis* SecA proteins. As export substrate, we used a variant of the alkaline phosphatase PhoB, which, on the basis of an amino acid exchange of leucine into glutamine on position 15 (PhoBL15Q) in the signal sequence, is exported only very inefficiently in the *B. subtilis* wild type. *B. subtilis* DB104 was transformed with the plasmids pCU3phoB or pCU3phoBL15Q, which contained the genes for the wild type PhoB or the variant PhoBL15Q as well as the plasmids pWAx that contained the altered secA *B. subtilis* genes. Using the strains thus obtained, LB medium was mixed with 0.5 mM IGTG and 0.2% xylose, it was inoculated at an $OD_{600}$ of 0.4, and the cultures were incubated for 4 hours at 37° C. Then, 2 ml of cells were separated from the supernatant by centrifugation, they were dissolved with 50 µl of lysis buffer and were boiled up in the same volume of 2× Laemmli sample buffer.

Figure 3:
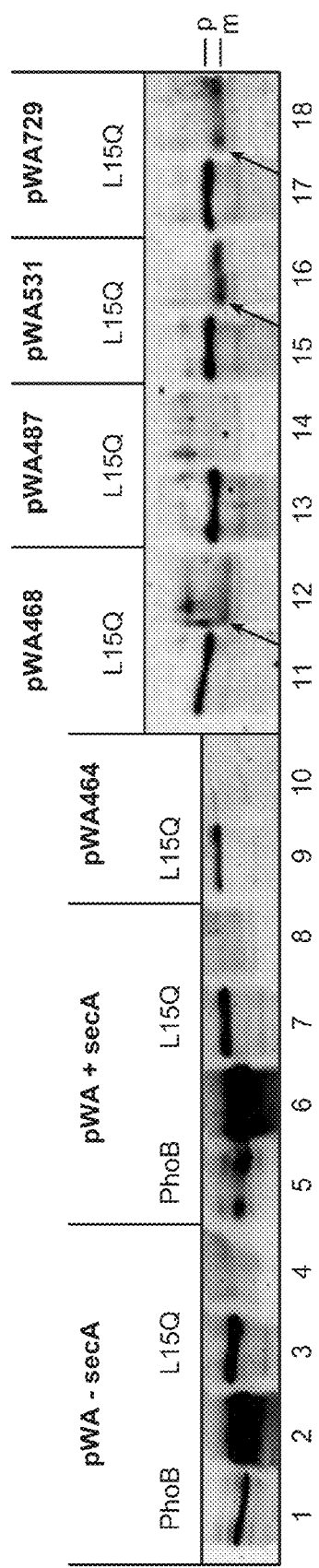
Figure 4:
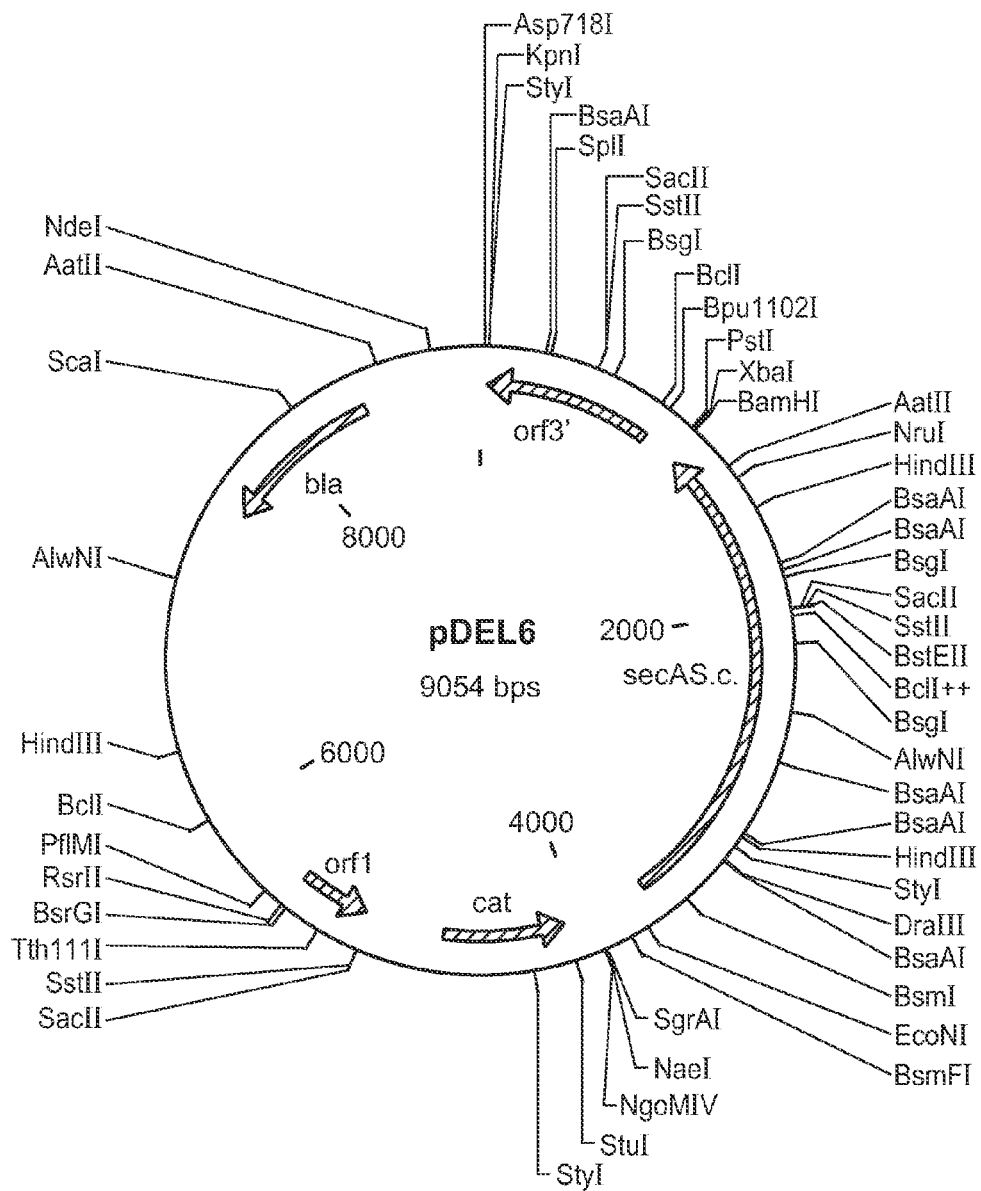

Proteins from the supernatants were precipitated overnight with 13% trichloracetic acid at 4° C., washed twice with 80% acetone and boiled up in 50 µl of Laemmli sample buffer. A volume corresponding to 0.2 OD cells of the cell extracts and a volume corresponding to 1.0 OD cells of the supernatants were applied upon a 12.5% SDS polyacrylamide gel and the PhoB was documented by means of PhoB-specific antibodies in Western Blot. The results are shown in FIG. 3.

BIBLIOGRAPHY

[in English]

......

4. Freudl, R. (1998): Protein Secretion in Gram-Positive Bacteria: Molecular Bases and Biotechnological Aspects. *Biospektrum* 4 (No. 1): 29-33.

......

[in English]

We claim:

1. An isolated nucleic acid comprising the nucleic acid sequence of SEQ ID NO: 3, and comprising at least one nucleotide change in the IRA-1 and/or IRA-2 encoding region (regulatory elements of SecA) selected from the group consisting of positions 1392, 1403, 1404, 1460, 1461, 1592 and 2186, wherein said nucleic acid encodes a mutant SecA which increases protein secretion.

2. The nucleic acid sequence of claim 1, wherein said nucleic acid sequence is obtained from a member of a bacterial family selected from the group of Bacillaceae, Staphylococcaceae, Enterobacteriaceae, and Corynebacteriaceae.

3. The nucleic acid sequence of claim 2, wherein said member of said bacterial family is selected from the group of *Bacillus subtilis, Bacillus licheniformis, Bacillus amyloliquefaciens, Staphylococcus carnosus, Escherichia coli*, and *Corynebacterium glutamicum*.

4. An expression vector comprising the nucleotide sequence of claim 1, wherein said vector further comprises at least one additional nucleic acid sequence wherein said additional nucleic acid sequence is selected from the group consisting of selection sequences, replication sequences, and integration sequences.

5. A host microorganism comprising the expression vector of claim 4.

6. The host microorganism of claim 5, wherein said expression vector replicates within said host microorganism.

7. The host microorganism of claim 5, wherein said host microorganism is selected from the group consisting of Gram-positive bacteria and Gram-negative bacteria.

8. The host microorganism of claim 5, wherein said host microorganism is a member of a bacterial family selected from the group of Bacillaceae, Staphylococcaceae, Enterobacteriaceae, and Corynebacteriaceae.

9. The host microorganism of claim 8, wherein said member of said bacterial family is selected from the group consisting of *Bacillus, Staphylococcus, Escherichia*, and *Corynebacterium*.

10. The host microorganism of claim 9, wherein said member of said bacterial family is selected from the group consisting of *Bacillus subtilis, Bacillus licheniformis, Bacillus amyloliquefaciens, Staphylococcus carnosus, Escherichia coli*, and *Corynebacterium glutamicum*.

11. A method for microbial production of proteins, comprising introducing the isolated nucleic acid of claim 1, which encodes a mutant SecA protein in a host microorganism under conditions such that a mutant microorganism is produced, and wherein said mutant microorganism expresses said mutant SecA protein.

12. The method of claim 11, wherein said mutant microorganism further expresses a protein at a high expression level, wherein said protein is selected from the group consisting of homologous proteins and heterologous proteins.

13. The method of claim 12, wherein said protein is recovered.

14. The method of claim 13, wherein said protein is selected from the group consisting of hormones, enzymes, growth factors, pharmaproteins, and cytokines.

15. The method of claim 14, wherein said enzyme is selected from the group consisting of proteases, amylases, carbohydrase, lipases, epimerases, tautomerases, mutases, transferases, kinases, and phosphatases.

* * * * *

SEQUENCE LISTING

<160> NUMBER OF SEQ ID NOS: 28

<210> SEQ ID NO 1
<211> LENGTH: 2535
<212> TYPE: DNA
<213> ORGANISM: Staphylococcus carnosus

<400> SEQUENCE: 1

| | | | | | |
|---|---|---|---|---|---|
| atgggttttt | taacaaaaat | tgttgacggc | aataagagag | aaatcaaacg | cctaagtaag | 60 |
| caagctgaca | agtaatctc | attagaagaa | gaaatgtcaa | ttcttactga | tgaagaaatt | 120 |
| agaaataaaa | caaaagcatt | ccaagaaaga | ttgcaagcag | aagaagatgt | aagcaaacaa | 180 |
| gataaaattt | tagaagaaat | attacctgaa | gcatttgcgc | ttgtccgtga | aggagctaaa | 240 |
| cgtgtattta | atatgacacc | ttatccagtt | caaatcatgg | gtggtatcgc | cattcataat | 300 |
| ggtgacattt | cagaaatgag | aacaggtgaa | ggtaaaacat | taactgcaac | gatgccgact | 360 |
| tatttaaacg | ccttagcagc | acgtggtgtg | catgttatta | cagtcaatga | atacttggca | 420 |
| agttctcaaa | gagaagaaat | ggccgagtta | tataatttcc | ttggtttatc | agtcggattg | 480 |
| aacttgaaca | gcttatcaac | agaacaaaag | cgtgaagctt | ataatgcaga | tattacgtat | 540 |
| agtacaaata | tgaattagg | cttcgactat | ttacgcgata | catggtgaa | ttattcagaa | 600 |
| gaacgtgtta | tgcgtccgct | tcatttcgct | atcattgatg | aggtcgactc | tatttaatc | 660 |
| gatgaagcgc | gtacaccatt | gattatttca | ggggaagctg | aaaaatcaac | atctctttat | 720 |
| acacaagcaa | atgttttcgc | taaaatgtta | aaagcagaag | atgattataa | ttatgatgaa | 780 |
| aaaacaaaat | cagtacaatt | aacagatcaa | ggtgctgata | agctgaacg | tatgttcaag | 840 |
| ttagataact | tatatgattt | gaaaaacgtt | gatattatca | cgcatatcaa | tacagcatta | 900 |
| cgtgctaact | atacattgca | acgcgatgta | gattacatgg | ttgtagatgg | agaagtattg | 960 |
| attgtcgacc | aatttacagg | tcgaacaatg | ccaggtcgtc | gattctctga | aggacttcac | 1020 |
| caagcgattg | aggctaaaga | aggggttcaa | attcaaaatg | aatctaaaac | aatggcttct | 1080 |
| atcacattcc | aaaactactt | ccgtatgtat | aataaattag | ccggtatgac | aggtactgct | 1140 |
| aaaacagagg | aagaagaatt | ccgtaacatt | tataatatga | cagttacaca | aattccaacg | 1200 |
| aaccgtcctg | ttcaacgtga | agatagacct | gacttgattt | tcatcagcca | aaaaggcaag | 1260 |
| ttcgatgctg | ttgttgaaga | tgttgttgaa | aaacataaaa | aaggccaacc | aattctttta | 1320 |
| ggtactgtag | cggttgaaac | aagtgaatac | atttcacaac | tattgaaaaa | acgcggtgtg | 1380 |
| cgtcatgatg | tcttaaacgc | taaaaaccat | gaacgcgaag | ctgaaatcgt | atctacagca | 1440 |
| ggtcaaaaag | gtgcagtcac | aatcgcaaca | aacatggctg | gtcgtggtac | cgatattaaa | 1500 |
| ttaggcgaag | gtgttgaaga | attaggcggc | cttgctgtta | ttggtacaga | acgtcatgaa | 1560 |
| tcacgccgta | tcgatgatca | gttgcgtggt | cgttctggac | gacaaggtga | ccgcggagaa | 1620 |
| agccgtttct | atttatcatt | acaagatgag | ttgatggtac | gtttcggttc | tgaacgtctg | 1680 |
| caaaaaatga | tgggccgatt | aggtatggat | gactctacac | cgattgaatc | aaaaatggta | 1740 |
| tctcgagctg | ttgaatctgc | acaaaaacgt | gttgaaggta | caacttcga | tgcacgtaaa | 1800 |
| cgtatcttag | aatacgatga | agttttacgt | aaacaacgtg | aaatcattta | tggtgaacgt | 1860 |
| aataatatta | tcgattcaga | atcaagttct | gaattagtca | ttacaatgat | acgctctaca | 1920 |
| ttagatcgtg | caatcagtta | ttatgtaaat | gaagaattgg | aagaaattga | ctatgcgccg | 1980 |
| tttattaatt | ttgtggaaga | tgttttcttg | cacgaaggtg | aagtcaaaga | agatgaaatc | 2040 |

-continued

```
aaaggtaaag gtaaagatcg tgaggatatt ttcgatacag tatgggctaa aattgaaaaa    2100
gcttatgaag cacaaaaagc caatatacc gaccaattca atgaattcga acgtatgatt    2160
ttattacgtt ctattgatgg aagatggaca gaccatatcg atacaatgga tcaattacgt    2220
caaggtatcc atttacgttc atacggtcaa caaaacccac ttcgcgacta tcaaaatgaa    2280
gggcaccaac tatttgatac aatgatggtc aatattgaag aagacgtcag caaatatatc    2340
ttgaaatcaa ttatcacagt agatgatgat attgaacgtg ataaagcaaa agaatatcaa    2400
ggacaacatg tatcagctga agatggaaaa gaaaaagtaa aaccgcaacc agttgttaaa    2460
gataatcaca tcggaagaaa tgatccttgt ccatgcggca gcggtaaaaa gtataaaaat    2520
tgctgcggta aatag                                                    2535
```

<210> SEQ ID NO 2
<211> LENGTH: 844
<212> TYPE: PRT
<213> ORGANISM: Staphylococcus carnosus

<400> SEQUENCE: 2

```
Met Gly Phe Leu Thr Lys Ile Val Asp Gly Asn Lys Arg Glu Ile Lys
1               5                   10                  15

Arg Leu Ser Lys Gln Ala Asp Lys Val Ile Ser Leu Glu Glu Glu Met
            20                  25                  30

Ser Ile Leu Thr Asp Glu Glu Ile Arg Asn Lys Thr Lys Ala Phe Gln
        35                  40                  45

Glu Arg Leu Gln Ala Glu Glu Asp Val Ser Lys Gln Asp Lys Ile Leu
    50                  55                  60

Glu Glu Ile Leu Pro Glu Ala Phe Ala Leu Val Arg Glu Gly Ala Lys
65                  70                  75                  80

Arg Val Phe Asn Met Thr Pro Tyr Pro Val Gln Ile Met Gly Gly Ile
                85                  90                  95

Ala Ile His Asn Gly Asp Ile Ser Glu Met Arg Thr Gly Glu Gly Lys
            100                 105                 110

Thr Leu Thr Ala Thr Met Pro Thr Tyr Leu Asn Ala Leu Ala Ala Arg
        115                 120                 125

Gly Val His Val Ile Thr Val Asn Glu Tyr Leu Ala Ser Ser Gln Arg
    130                 135                 140

Glu Glu Met Ala Glu Leu Tyr Asn Phe Leu Gly Leu Ser Val Gly Leu
145                 150                 155                 160

Asn Leu Asn Ser Leu Ser Thr Glu Gln Lys Arg Glu Ala Tyr Asn Ala
                165                 170                 175

Asp Ile Thr Tyr Ser Thr Asn Asn Glu Leu Gly Phe Asp Tyr Leu Arg
            180                 185                 190

Asp Asn Met Val Asn Tyr Ser Glu Glu Arg Val Met Arg Pro Leu His
        195                 200                 205

Phe Ala Ile Ile Asp Glu Val Asp Ser Ile Leu Ile Asp Glu Ala Arg
    210                 215                 220

Thr Pro Leu Ile Ile Ser Gly Glu Ala Glu Lys Ser Thr Ser Leu Tyr
225                 230                 235                 240

Thr Gln Ala Asn Val Phe Ala Lys Met Leu Lys Ala Glu Asp Asp Tyr
                245                 250                 255

Asn Tyr Asp Glu Lys Thr Lys Ser Val Gln Leu Thr Asp Gln Gly Ala
            260                 265                 270

Asp Lys Ala Glu Arg Met Phe Lys Leu Asp Asn Leu Tyr Asp Leu Lys
```

```
                275                 280                 285
Asn Val Asp Ile Ile Thr His Ile Asn Thr Ala Leu Arg Ala Asn Tyr
290                 295                 300
Thr Leu Gln Arg Asp Val Asp Tyr Met Val Val Asp Gly Glu Val Leu
305                 310                 315                 320
Ile Val Asp Gln Phe Thr Gly Arg Thr Met Pro Gly Arg Arg Phe Ser
            325                 330                 335
Glu Gly Leu His Gln Ala Ile Glu Ala Lys Glu Gly Val Gln Ile Gln
                340                 345                 350
Asn Glu Ser Lys Thr Met Ala Ser Ile Thr Phe Gln Asn Tyr Phe Arg
            355                 360                 365
Met Tyr Asn Lys Leu Ala Gly Met Thr Gly Thr Ala Lys Thr Glu Glu
        370                 375                 380
Glu Glu Phe Arg Asn Ile Tyr Asn Met Thr Val Thr Gln Ile Pro Thr
385                 390                 395                 400
Asn Arg Pro Val Gln Arg Glu Asp Arg Pro Asp Leu Ile Phe Ile Ser
                405                 410                 415
Gln Lys Gly Lys Phe Asp Ala Val Val Glu Asp Val Val Glu Lys His
            420                 425                 430
Lys Lys Gly Gln Pro Ile Leu Leu Gly Thr Val Ala Val Glu Thr Ser
        435                 440                 445
Glu Tyr Ile Ser Gln Leu Leu Lys Lys Arg Gly Val Arg His Asp Val
        450                 455                 460
Leu Asn Ala Lys Asn His Glu Arg Glu Ala Glu Ile Val Ser Thr Ala
465                 470                 475                 480
Gly Gln Lys Gly Ala Val Thr Ile Ala Thr Asn Met Ala Gly Arg Gly
                485                 490                 495
Thr Asp Ile Lys Leu Gly Glu Gly Val Glu Glu Leu Gly Gly Leu Ala
            500                 505                 510
Val Ile Gly Thr Glu Arg His Glu Ser Arg Arg Ile Asp Asp Gln Leu
        515                 520                 525
Arg Gly Arg Ser Gly Arg Gln Gly Asp Arg Gly Glu Ser Arg Phe Tyr
530                 535                 540
Leu Ser Leu Gln Asp Glu Leu Met Val Arg Phe Gly Ser Glu Arg Leu
545                 550                 555                 560
Gln Lys Met Met Gly Arg Leu Gly Met Asp Asp Ser Thr Pro Ile Glu
                565                 570                 575
Ser Lys Met Val Ser Arg Ala Val Glu Ser Ala Gln Lys Arg Val Glu
            580                 585                 590
Gly Asn Asn Phe Asp Ala Arg Lys Arg Ile Leu Glu Tyr Asp Glu Val
        595                 600                 605
Leu Arg Lys Gln Arg Glu Ile Ile Tyr Gly Glu Arg Asn Asn Ile Ile
        610                 615                 620
Asp Ser Glu Ser Ser Ser Glu Leu Val Ile Thr Met Ile Arg Ser Thr
625                 630                 635                 640
Leu Asp Arg Ala Ile Ser Tyr Tyr Val Asn Glu Glu Leu Glu Glu Ile
                645                 650                 655
Asp Tyr Ala Pro Phe Ile Asn Phe Val Glu Asp Val Phe Leu His Glu
            660                 665                 670
Gly Glu Val Lys Glu Asp Glu Ile Lys Gly Lys Gly Lys Asp Arg Glu
        675                 680                 685
Asp Ile Phe Asp Thr Val Trp Ala Lys Ile Glu Lys Ala Tyr Glu Ala
    690                 695                 700
```

```
Gln Lys Ala Asn Ile Pro Asp Gln Phe Asn Glu Phe Glu Arg Met Ile
705                 710                 715                 720

Leu Leu Arg Ser Ile Asp Gly Arg Trp Thr Asp His Ile Asp Thr Met
            725                 730                 735

Asp Gln Leu Arg Gln Gly Ile His Leu Arg Ser Tyr Gly Gln Gln Asn
        740                 745                 750

Pro Leu Arg Asp Tyr Gln Asn Glu Gly His Gln Leu Phe Asp Thr Met
    755                 760                 765

Met Val Asn Ile Glu Glu Asp Val Ser Lys Tyr Ile Leu Lys Ser Ile
770                 775                 780

Ile Thr Val Asp Asp Ile Glu Arg Asp Lys Ala Lys Glu Tyr Gln
785                 790                 795                 800

Gly Gln His Val Ser Ala Glu Asp Gly Lys Glu Lys Val Lys Pro Gln
                805                 810                 815

Pro Val Val Lys Asp Asn His Ile Gly Arg Asn Asp Pro Cys Pro Cys
            820                 825                 830

Gly Ser Gly Lys Lys Tyr Lys Asn Cys Cys Gly Lys
        835                 840

<210> SEQ ID NO 3
<211> LENGTH: 2526
<212> TYPE: DNA
<213> ORGANISM: Bacillus subtilis

<400> SEQUENCE: 3
atgcttggaa ttttaaataa aatgtttgat ccaacaaaac gtacgctgaa tagatacgaa      60
aaaattgcta acgatattga tgcgattcgc ggagactatg aaaatctctc tgacgacgca     120
ttgaaacata aaacaattga atttaaagag cgtcttgaaa aaggggcgac aacggatgat     180
cttcttgttg aagctttcgc tgttgttcga gaagcttcac gccgcgtaac aggcatgttt     240
ccgtttaaag tccagctcat gggggggcgtg gcgcttcatg acggaaatat agcggaaatg     300
aaaacagggg aagggaaaac attaacgtct accctgcctg tttatttaaa tgcgttaacc     360
ggtaaaggcg tacacgtcgt gactgtcaac gaatacttgg caagccgtga cgctgagcaa     420
atggggaaaa tttttcgagtt tctcggtttg actgtcggtt tgaatttaaa ctcaatgtca     480
aaagacgaaa acgggaagc ttatgccgct gatattactt actccacaaa caacgagctt     540
ggcttcgact atttgcgtga caatatggtt ctttataaag agcagatggt tcagcgcccg     600
cttcattttg cggtaataga tgaagttgac tctatttaa ttgatgaagc aagaacaccg     660
cttatcattt ctggacaagc tgcaaaatcc actaagctgt acgtacaggc aaatgctttt     720
gtccgcacgt taaagcgga aaggattac acgtacgata tcaaaacaaa agctgtacag     780
cttactgaag aaggaatgac gaaggcggaa aaagcattcg gcatcgataa cctctttgat     840
gtgaagcatg tcgcgctcaa ccaccatatc aaccaggcct aaaagctca cgttgcgatg     900
caaaaggacg ttgactatgt agtggaagac ggacaggttg ttattgttga ttccttcacg     960
ggacgtctga tgaaaggccg ccgctacagt gaggggcttc accaagcgat gaagcaaag    1020
gaagggcttg agattcaaaa cgaaagcatg accttggcga cgattacgtt ccaaaactac    1080
ttccgaatgt acgaaaaact tgccggtatg acgggtacag ctaagacaga ggaagaagaa    1140
ttccgcaaca tctacaacat gcaggttgtc acgatcccta ccaacaggcc tgttgtccgt    1200
gatgaccgcc cggatttaat ttaccgcacg atggaaggaa agtttaaggc agttgcggag    1260
gatgtcgcac agcgttacat gacgggacag cctgttctag tcggtacggt tgccgttgaa    1320
```

-continued

```
acatctgaat tgatttctaa gctgcttaaa aacaaaggaa ttccgcatca agtgttaaat    1380
gccaaaaacc atgaacgtga agcgcagatc attgaagagg ccggccaaaa aggcgcagtt    1440
acgattgcga ctaacatggc ggggcgcgga acggacatta agcttggcga aggtgtaaaa    1500
gagcttggcg ggctcgctgt agtcggaaca gaacgacatg aatcacgccg gattgacaat    1560
cagcttcgag gtcgttccgg acgtcaggga gacccgggga ttactcaatt ttatctttct    1620
atggaagatg aattgatgcg cagattcgga gctgagcgga caatggcgat gcttgaccgc    1680
ttcggcatgg acgactctac tccaatccaa agcaaatgg tatctcgcgc ggttgaatcg    1740
tctcaaaaac gcgtcgaagg caataacttc gattcgcgta acagcttct gcaatatgat    1800 gatgttctcc gccagcagcg tgaggtcatt tataagcagc gctttgaagt cattgactct    1860
gaaaacctgc gtgaaatcgt tgaaaatatg atcaagtctt ctctcgaacg cgcaattgca    1920
gcctatacgc caagagaaga gcttcctgag gagtggaagc ttgacggtct agttgatctt    1980
atcaacacaa cttatcttga tgaaggtgca cttgagaaga gcgatatctt cggcaaagaa    2040
ccggatgaaa tgcttgagct cattatggat cgcatcatca caaaatataa tgagaaggaa    2100
gagcaattcg gcaaagagca aatgcgcgaa ttcgaaaaag ttatcgttct tcgtgccgtt    2160
gattctaaat ggatggatca tattgatgcg atggatcagc tccgccaagg gattcacctt    2220
cgtgcttacg cgcagacgaa cccgcttcgt gagtatcaaa tggaaggttt tgcgatgttt    2280
gagcatatga ttgaatcaat tgaggacgaa gtcgcaaaat ttgtgatgaa agctgagatt    2340
gaaaacaatc tggagcgtga agaggttgta caaggtcaaa caacagctca tcagccgcaa    2400
gaaggcgacg ataacaaaaa agcaaagaaa gcaccggttc gcaaagtggt tgatatcgga    2460
cgaaatgccc catgccactg cggaagcggg aaaaaatata aaaattgctg cggccgtact    2520
gaatag                                                             2526
```

<210> SEQ ID NO 4
<211> LENGTH: 841
<212> TYPE: PRT
<213> ORGANISM: Bacillus subtilis

<400> SEQUENCE: 4

```
Met Leu Gly Ile Leu Asn Lys Met Phe Asp Pro Thr Lys Arg Thr Leu
1               5                   10                  15

Asn Arg Tyr Glu Lys Ile Ala Asn Asp Ile Asp Ala Ile Arg Gly Asp
            20                  25                  30

Tyr Glu Asn Leu Ser Asp Asp Ala Leu Lys His Lys Thr Ile Glu Phe
        35                  40                  45

Lys Glu Arg Leu Glu Lys Gly Ala Thr Thr Asp Asp Leu Leu Val Glu
    50                  55                  60

Ala Phe Ala Val Val Arg Glu Ala Ser Arg Arg Val Thr Gly Met Phe
65                  70                  75                  80

Pro Phe Lys Val Gln Leu Met Gly Gly Val Ala Leu His Asp Gly Asn
                85                  90                  95

Ile Ala Glu Met Lys Thr Gly Glu Gly Lys Thr Leu Thr Ser Thr Leu
            100                 105                 110

Pro Val Tyr Leu Asn Ala Leu Thr Gly Lys Gly Val His Val Val Thr
        115                 120                 125

Val Asn Glu Tyr Leu Ala Ser Arg Asp Ala Glu Gln Met Gly Lys Ile
    130                 135                 140

Phe Glu Phe Leu Gly Leu Thr Val Gly Leu Asn Leu Asn Ser Met Ser
```

-continued

```
            145                 150                 155                 160
        Lys Asp Glu Lys Arg Glu Ala Tyr Ala Ala Asp Ile Thr Tyr Ser Thr
                        165                 170                 175
        Asn Asn Glu Leu Gly Phe Asp Tyr Leu Arg Asp Asn Met Val Leu Tyr
                    180                 185                 190
        Lys Glu Gln Met Val Gln Arg Pro Leu His Phe Ala Val Ile Asp Glu
                    195                 200                 205
        Val Asp Ser Ile Leu Ile Asp Glu Ala Arg Thr Pro Leu Ile Ile Ser
            210                 215                 220
        Gly Gln Ala Ala Lys Ser Thr Lys Leu Tyr Val Gln Ala Asn Ala Phe
        225                 230                 235                 240
        Val Arg Thr Leu Lys Ala Glu Lys Asp Tyr Thr Tyr Asp Ile Lys Thr
                        245                 250                 255
        Lys Ala Val Gln Leu Thr Glu Glu Gly Met Thr Lys Ala Glu Lys Ala
                    260                 265                 270
        Phe Gly Ile Asp Asn Leu Phe Asp Val Lys His Val Ala Leu Asn His
                    275                 280                 285
        His Ile Asn Gln Ala Leu Lys Ala His Val Ala Met Gln Lys Asp Val
                290                 295                 300
        Asp Tyr Val Val Glu Asp Gly Gln Val Ile Val Asp Ser Phe Thr
        305                 310                 315                 320
        Gly Arg Leu Met Lys Gly Arg Arg Tyr Ser Glu Gly Leu His Gln Ala
                        325                 330                 335
        Ile Glu Ala Lys Glu Gly Leu Glu Ile Gln Asn Glu Ser Met Thr Leu
                    340                 345                 350
        Ala Thr Ile Thr Phe Gln Asn Tyr Phe Arg Met Tyr Glu Lys Leu Ala
                    355                 360                 365
        Gly Met Thr Gly Thr Ala Lys Thr Glu Glu Glu Phe Arg Asn Ile
                370                 375                 380
        Tyr Asn Met Gln Val Val Thr Ile Pro Thr Asn Arg Pro Val Val Arg
        385                 390                 395                 400
        Asp Asp Arg Pro Asp Leu Ile Tyr Arg Thr Met Glu Gly Lys Phe Lys
                        405                 410                 415
        Ala Val Ala Glu Asp Val Ala Gln Arg Tyr Met Thr Gly Gln Pro Val
                    420                 425                 430
        Leu Val Gly Thr Val Ala Val Glu Thr Ser Glu Leu Ile Ser Lys Leu
                    435                 440                 445
        Leu Lys Asn Lys Gly Ile Pro His Gln Val Leu Asn Ala Lys Asn His
                450                 455                 460
        Glu Arg Glu Ala Gln Ile Ile Glu Glu Ala Gly Gln Lys Gly Ala Val
        465                 470                 475                 480
        Thr Ile Ala Thr Asn Met Ala Gly Arg Gly Thr Asp Ile Lys Leu Gly
                        485                 490                 495
        Glu Gly Val Lys Glu Leu Gly Gly Leu Ala Val Gly Thr Glu Arg
                    500                 505                 510
        His Glu Ser Arg Arg Ile Asp Asn Gln Leu Arg Gly Arg Ser Gly Arg
                    515                 520                 525
        Gln Gly Asp Pro Gly Ile Thr Gln Phe Tyr Leu Ser Met Glu Asp Glu
                530                 535                 540
        Leu Met Arg Arg Phe Gly Ala Glu Arg Thr Met Ala Met Leu Asp Arg
        545                 550                 555                 560
        Phe Gly Met Asp Asp Ser Thr Pro Ile Gln Ser Lys Met Val Ser Arg
                        565                 570                 575
```

-continued

Ala Val Glu Ser Ser Gln Lys Arg Val Glu Gly Asn Asn Phe Asp Ser
            580                 585                 590

Arg Lys Gln Leu Leu Gln Tyr Asp Asp Val Leu Arg Gln Gln Arg Glu
        595                 600                 605

Val Ile Tyr Lys Gln Arg Phe Glu Val Ile Asp Ser Glu Asn Leu Arg
    610                 615                 620

Glu Ile Val Glu Asn Met Ile Lys Ser Ser Leu Glu Arg Ala Ile Ala
625                 630                 635                 640

Ala Tyr Thr Pro Arg Glu Glu Leu Pro Glu Glu Trp Lys Leu Asp Gly
            645                 650                 655

Leu Val Asp Leu Ile Asn Thr Thr Tyr Leu Asp Glu Gly Ala Leu Glu
            660                 665                 670

Lys Ser Asp Ile Phe Gly Lys Glu Pro Asp Glu Met Leu Glu Leu Ile
        675                 680                 685

Met Asp Arg Ile Ile Thr Lys Tyr Asn Glu Lys Glu Glu Gln Phe Gly
    690                 695                 700

Lys Glu Gln Met Arg Glu Phe Glu Lys Val Ile Val Leu Arg Ala Val
705                 710                 715                 720

Asp Ser Lys Trp Met Asp His Ile Asp Ala Met Asp Gln Leu Arg Gln
            725                 730                 735

Gly Ile His Leu Arg Ala Tyr Ala Gln Thr Asn Pro Leu Arg Glu Tyr
            740                 745                 750

Gln Met Glu Gly Phe Ala Met Phe Glu His Met Ile Glu Ser Ile Glu
        755                 760                 765

Asp Glu Val Ala Lys Phe Val Met Lys Ala Glu Ile Glu Asn Asn Leu
    770                 775                 780

Glu Arg Glu Glu Val Val Gln Gly Gln Thr Thr Ala His Gln Pro Gln
785                 790                 795                 800

Glu Gly Asp Asp Asn Lys Lys Ala Lys Lys Ala Pro Val Arg Lys Val
            805                 810                 815

Val Asp Ile Gly Arg Asn Ala Pro Cys His Cys Gly Ser Gly Lys Lys
            820                 825                 830

Tyr Lys Asn Cys Cys Gly Arg Thr Glu
        835                 840

```
<210> SEQ ID NO 5
<211> LENGTH: 29
<212> TYPE: DNA
<213> ORGANISM: Artificial Sequence
<220> FEATURE:
<223> OTHER INFORMATION: synthetic primer

<400> SEQUENCE: 5
cgggatccca aaggagcgaa cagaatggg                                29

<210> SEQ ID NO 6
<211> LENGTH: 34
<212> TYPE: DNA
<213> ORGANISM: Artificial Sequence
<220> FEATURE:
<223> OTHER INFORMATION: synthetic primer

<400> SEQUENCE: 6
acatgcatgc atacaactta ctatttaccg cagc                          34

<210> SEQ ID NO 7
<211> LENGTH: 18
```

```
<212> TYPE: DNA
<213> ORGANISM: Artificial Sequence
<220> FEATURE:
<223> OTHER INFORMATION: synthetic primer

<400> SEQUENCE: 7
aactgcaacg atgccgac                                              18

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
gtgctgataa agctgaacg                                             19

<210> SEQ ID NO 9
<211> LENGTH: 18
<212> TYPE: DNA
<213> ORGANISM: Artificial Sequence
<220> FEATURE:
<223> OTHER INFORMATION: synthetic primer

<400> SEQUENCE: 9
gacaaggtga ccgcggag                                              18

<210> SEQ ID NO 10
<211> LENGTH: 18
<212> TYPE: DNA
<213> ORGANISM: Artificial Sequence
<220> FEATURE:
<223> OTHER INFORMATION: synthetic primer

<400> SEQUENCE: 10
aattccaacg aaccgtcc                                              18

<210> SEQ ID NO 11
<211> LENGTH: 18
<212> TYPE: DNA
<213> ORGANISM: Artificial Sequence
<220> FEATURE:
<223> OTHER INFORMATION: synthetic primer

<400> SEQUENCE: 11
aaggtaaaga tcgtgagg                                              18

<210> SEQ ID NO 12
<211> LENGTH: 18
<212> TYPE: DNA
<213> ORGANISM: Artificial Sequence
<220> FEATURE:
<223> OTHER INFORMATION: synthetic primer

<400> SEQUENCE: 12
ctgttcaagt tcaatccg                                              18

<210> SEQ ID NO 13
<211> LENGTH: 39
<212> TYPE: DNA
<213> ORGANISM: Artificial Sequence
<220> FEATURE:
<223> OTHER INFORMATION: synthetic primer

<400> SEQUENCE: 13
```
gtgttaaatg ccaaaaacca agaacgtgaa gcgcagatc        39

<210> SEQ ID NO 14
<211> LENGTH: 39
<212> TYPE: DNA
<213> ORGANISM: Artificial Sequence
<220> FEATURE:
<223> OTHER INFORMATION: synthetic primer

<400> SEQUENCE: 14
gatctgcgct tcacgttctt ggttttggc atttaacac         39

<210> SEQ ID NO 15
<211> LENGTH: 38
<212> TYPE: DNA
<213> ORGANISM: Artificial Sequence
<220> FEATURE:
<223> OTHER INFORMATION: synthetic primer

<400> SEQUENCE: 15
ccatgaacgt gaagttcaga tcattgaaga ggccggcc         38

<210> SEQ ID NO 16
<211> LENGTH: 38
<212> TYPE: DNA
<213> ORGANISM: Artificial Sequence
<220> FEATURE:
<223> OTHER INFORMATION: synthetic primer

<400> SEQUENCE: 16
ggccggcctc ttcaatgatc tgaacttcac gttcatgg         38

<210> SEQ ID NO 17
<211> LENGTH: 33
<212> TYPE: DNA
<213> ORGANISM: Artificial Sequence
<220> FEATURE:
<223> OTHER INFORMATION: synthetic primer

<400> SEQUENCE: 17
cgattgcgac taacatggtt gggcgcggaa cgg              33

<210> SEQ ID NO 18
<211> LENGTH: 33
<212> TYPE: DNA
<213> ORGANISM: Artificial Sequence
<220> FEATURE:
<223> OTHER INFORMATION: synthetic primer

<400> SEQUENCE: 18
ccgttccgcg cccaaccatg ttagtcgcaa tcg              33

<210> SEQ ID NO 19
<211> LENGTH: 30
<212> TYPE: DNA
<213> ORGANISM: Artificial Sequence
<220> FEATURE:
<223> OTHER INFORMATION: synthetic primer

<400> SEQUENCE: 19
ccggacgtca gggagccccg gggattactc                  30

<210> SEQ ID NO 20
<211> LENGTH: 30
<212> TYPE: DNA
<213> ORGANISM: Artificial Sequence
<220> FEATURE:
<223> OTHER INFORMATION: synthetic primer

<400> SEQUENCE: 20
gagtaatccc cggggctccc tgacgtccgg                                    30

<210> SEQ ID NO 21
<211> LENGTH: 41
<212> TYPE: DNA
<213> ORGANISM: Artificial Sequence
<220> FEATURE:
<223> OTHER INFORMATION: synthetic primer

<400> SEQUENCE: 21
ggatggatca tattgttgcg atggatcagc tccgccaagg g                       41

<210> SEQ ID NO 22
<211> LENGTH: 41
<212> TYPE: DNA
<213> ORGANISM: Artificial Sequence
<220> FEATURE:
<223> OTHER INFORMATION: synthetic primer

<400> SEQUENCE: 22
cccttggcgg agctgatcca tcgcaacaat atgatccatc c                       41

<210> SEQ ID NO 23
<211> LENGTH: 18
<212> TYPE: DNA
<213> ORGANISM: Artificial Sequence
<220> FEATURE:
<223> OTHER INFORMATION: synthetic primer

<400> SEQUENCE: 23
gtacagctaa gacagagg                                                 18

<210> SEQ ID NO 24
<211> LENGTH: 18
<212> TYPE: DNA
<213> ORGANISM: Artificial Sequence
<220> FEATURE:
<223> OTHER INFORMATION: synthetic primer

<400> SEQUENCE: 24
ttgaccgctt cggcatgg                                                 18

<210> SEQ ID NO 25
<211> LENGTH: 19
<212> TYPE: DNA
<213> ORGANISM: Artificial Sequence
<220> FEATURE:
<223> OTHER INFORMATION: synthetic primer

<400> SEQUENCE: 25
aagggattca ccttcgtgc                                                19

<210> SEQ ID NO 26
<211> LENGTH: 18
<212> TYPE: DNA
<213> ORGANISM: Artificial Sequence
<220> FEATURE:
<223> OTHER INFORMATION: synthetic primer

<400> SEQUENCE: 26
tttccttcca tcgtgcgg                                                 18

```
<210> SEQ ID NO 27
<211> LENGTH: 18
<212> TYPE: DNA
<213> ORGANISM: Artificial Sequence
<220> FEATURE:
<223> OTHER INFORMATION: synthetic primer

<400> SEQUENCE: 27
ttcagtaagc tgtacagc                                                 18

<210> SEQ ID NO 28
<211> LENGTH: 18
<212> TYPE: DNA
<213> ORGANISM: Artificial Sequence
<220> FEATURE:
<223> OTHER INFORMATION: synthetic primer

<400> SEQUENCE: 28
tttccgtcat gaagcgcc                                                 18
```